US012565500B2

(12) United States Patent
Marx et al.

(10) Patent No.: US 12,565,500 B2
(45) Date of Patent: Mar. 3, 2026

(54) SUBSTITUTED PYRROLO[1,2-B]PYRIDAZINES AND PYRROLO[2,1-F][1,2,4]TRIAZINES AS BTK INHIBITORS

(71) Applicant: BIOGEN MA INC., Cambridge, MA (US)

(72) Inventors: Isaac Marx, Arlington, MA (US); Jürgen Schulz, Boston, MA (US); Brian T. Hopkins, Newton, MA (US); Bin Ma, Arlington, MA (US); Robin Prince, Sharon, MA (US); Marta Nevalainen, Holliston, MA (US)

(73) Assignee: BIOGEN MA INC., Cambridge, MA (US)

( * ) Notice: Subject to any disclaimer, the term of this patent is extended or adjusted under 35 U.S.C. 154(b) by 918 days.

(21) Appl. No.: 17/773,471

(22) PCT Filed: Oct. 29, 2020

(86) PCT No.: PCT/US2020/057919

§ 371 (c)(1),
(2) Date: Apr. 29, 2022

(87) PCT Pub. No.: WO2021/087086

PCT Pub. Date: May 6, 2021

(65) Prior Publication Data

US 2022/0411429 A1 Dec. 29, 2022

Related U.S. Application Data

(60) Provisional application No. 62/928,062, filed on Oct. 30, 2019.

(51) Int. Cl.

| | |
|---|---|
| ***A61K 31/4985*** | (2006.01) |
| ***A61K 31/53*** | (2006.01) |
| ***C07D 237/26*** | (2006.01) |
| ***C07D 253/10*** | (2006.01) |
| ***C07D 487/04*** | (2006.01) |
| ***C07D 519/00*** | (2006.01) |

(52) U.S. Cl.
CPC ......... *C07D 487/04* (2013.01); *C07D 519/00* (2013.01)

(58) Field of Classification Search
CPC ................ A61K 31/4985; A61K 31/53; C07D 237/26; C07D 253/10
USPC .......................... 514/243, 248; 544/183, 235
See application file for complete search history.

(56) References Cited

U.S. PATENT DOCUMENTS

| | | | |
|---|---|---|---|
| 2018/0194762 | A1 | 7/2018 | Atallah |
| 2019/0330226 | A1 | 10/2019 | Lindsley et al. |

FOREIGN PATENT DOCUMENTS

| | | | |
|---|---|---|---|
| WO | 2014/064131 A2 | 5/2014 |
| WO | 2014/076104 A1 | 5/2014 |
| WO | 2016/057500 A1 | 10/2014 |
| WO | 2018/119036 A1 | 6/2018 |
| WO | 2019/034009 A1 | 2/2019 |

OTHER PUBLICATIONS

International Search Report and Written Opinion for Application No. PCT/US2020/057919, dated Jan. 20, 2021, 8 pages.

*Primary Examiner* — Douglas M Willis
(74) *Attorney, Agent, or Firm* — McCarter & English, LLP; Xin Zhang

(57) ABSTRACT

Provided are compounds of Formula (I) or pharmaceutically acceptable salts thereof, wherein ring A, $R^3$, $R^4$, $R^5$, $R^6$, $A^1$, $B^1$, $B^2$, $Q^1$ and $Q^2$ are as defined herein; and methods for their use and production.

(I)

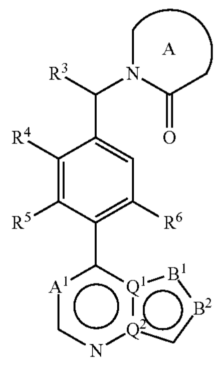

19 Claims, No Drawings

SUBSTITUTED PYRROLO[1,2-B]PYRIDAZINES AND PYRROLO[2,1-F][1,2,4]TRIAZINES AS BTK INHIBITORS

RELATED APPLICATIONS

This application is a 35 U.S.C. § 371 national stage filing of International Application No. PCT/US2020/057919, filed on Oct. 29, 2020, which in turn claims the benefit of the filing date, under 35 U.S.C. § 119(e), of U.S. Provisional Patent Application No. 62/928,062, filed on Oct. 30, 2019. The entire contents of the aforementioned applications are incorporated herein by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I):

(I)

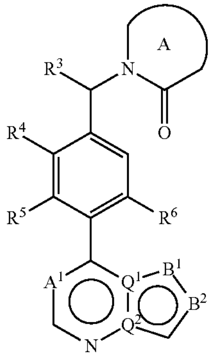

or a pharmaceutically acceptable salt thereof, wherein:

$A^1$ is selected from $CR^7$ and N;

$B^1$ and $B^2$ are each independently selected from $CR^8$, N, and $NR^8$;

one of $Q^1$ and $Q^2$ is N, and the other one is C;

Ring A is selected from 3- to 7-membered monocyclic heterocyclyl and 7- to 10-membered bicyclic heterocyclyl; wherein Ring A is optionally substituted with one or more $R^{100}$;

$R^{100}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —CN, $—C(O)R^{100a}$, $—C(O)_2R^{100a}$; $—C(O)N(R^{100a})_2$, $—N(R^{100a})_2$, $—N(R^{100a})C(O)R^{100a}$, $—N(R^{100a})C(O)_2R^{100a}$, $—N(R^{100a})C(O)N(R^{100a})_2$, $—N(R^{100a})S(O)_2R^{100a}$, $—OR^{100a}$, $—OC(O)R^{100a}$, $—OC(O)N(R^{100a})_2$, $—SR^{100a}$, $—S(O)R^{100a}$, $—S(O)_2R^{100a}$, $—S(O)N(R^{100a})_2$, $—S(O)_2N(R^{100a})_2$; wherein the $C_{1-6}$alkyl, $C_{2-6}$alkenyl, $C_{2-6}$alkynyl, 3- to 7-membered monocyclic carbocyclyl, and 4- to 6-membered monocyclic heterocyclyl represented by $R^{100}$ are each optionally substituted with one or more $R^{150}$; or two $R^{100}$ taken together with their intervening atom, form a 4- to 6-membered monocyclic heterocyclyl or 3- to 7-membered monocyclic carbocyclyl, each of which is optionally substituted with one or more $R^{150}$;

$R^{100a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{100a}$ are each optionally substituted with one or more $R^{150}$;

$R^{150}$, for each occurrence, is independently selected from $C_{1-6}$ alkyl, halogen and $—OR^{150a}$;

$R^{150a}$ is H or $C_{1-6}$ alkyl;

$R^3$ is selected from H, $C_{1-6}$ alkyl, $C_{2-6}$ alkenyl, $C_{2-6}$ alkynyl, $—C(O)N(R^{3a})_2$, $—C(O)OR^{3a}$, and $—C(O)R^{3a}$, wherein the $C_{1-6}$ alkyl, $C_{2-6}$ alkenyl, and $C_{2-6}$ alkynyl represented by $R^3$ are each optionally substituted with one or more $R^{30}$;

$R^{3a}$, for each occurrence, is independently selected from H, $C_{1-6}$ alkyl, $C_{2-6}$ alkenyl, $C_{2-6}$ alkynyl, wherein the $C_{1-6}$ alkyl, $C_{2-6}$ alkenyl, and $C_{2-6}$ alkynyl represented by $R^{3a}$ are each optionally substituted with one or more $R^{30}$;

$R^{30}$, for each occurrence, is independently selected from halogen, —$OR^{30a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{30a}$ is H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl;

$R^4$ is selected from H, $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —NO2, —CN, —$OR^{4a}$, —$SR^{4a}$, —$N(R^{4a})_2$, —$C(O)R^{4a}$, —$C(O)OR^{4a}$, —$S(O)R^{4a}$, —$S(O)_2R^{4a}$, —$C(O)N(R^{4a})_2$, —$SO_2N(R^{4a})_2$, —$OC(O)R^{4a}$, —$N(R)C(O)R^{4a}$, —$N(R)C(O)OR^{4a}$, —$N(R)SO_2R^{4a}$, and —$OC(O)N(R^{4a})_2$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^4$ are each optionally substituted with one or more $R^{40}$;

$R^{4a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{4a}$ are each optionally substituted with one or more $R^{40}$;

$R^{40}$, for each occurrence, is independently selected from halogen, —$OR^{40a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{30}$ are each optionally substituted with one or more $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl are each optionally substituted with one or more $R^{45}$;

$R^{45}$, for each occurrence, is independently selected from $C_{1-6}$ alkyl, halogen and —$OR^{45a}$;

$R^{45a}$ is H or $C_{1-6}$ alkyl;

or alternatively $R^3$ and $R^4$, taken together with their intervening atoms form Ring B that is selected from 5- to 7-membered monocyclic carbocyclyl and 5- to 7-membered monocyclic heterocyclyl having 1-2 heteroatoms independently selected from O, N and S; wherein Ring B is optionally substituted with one or more $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —$C(O)R^{300a}$, —$OR^{300a}$, and —$S(O)_2R^{300a}$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more $R^{350}$;

$R^{350}$, for each occurrence, is independently selected from $C_{1-6}$ alkyl, halogen, —CN, —$C(O)R^{350a}$, —$C(O)N(R^{350a})_2$, —$C(R^{350a})_2N(R^{350a})_2$, and —$OR^{350a}$.

$R^{350a}$, for each occurrence, is independently H or $C_{1-6}$ alkyl optionally substituted with one to three halogen;

$R^5$ is selected from H, $C_{1-6}$ alkyl, $C_{2-6}$ alkenyl, $C_{2-6}$ alkynyl, halogen, and —$OR^{5a}$; wherein the $C_{1-6}$ alkyl, $C_{2-6}$ alkenyl, and $C_{2-6}$ alkynyl represented by $R^5$ are optionally substituted with one or more halogen;

$R^{5a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl represented by $R^{5a}$ are each optionally substituted with one or more halogen;

$R^6$ is selected from H, $C_{1-6}$ alkyl, $C_{2-6}$ alkenyl, $C_{2-6}$ alkynyl, halogen, —$OR^{6a}$; wherein the $C_{1-6}$ alkyl, $C_{2-6}$ alkenyl and $C_{2-6}$ alkynyl represented by $R^6$ are each optionally substituted with one or more halogen;

$R^{6a}$ is H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{6a}$ are each optionally substituted with one or more halogen;

$R^7$ is selected from H, $C_{1-6}$ alkyl, $C_{2-6}$ alkenyl, $C_{2-6}$ alkynyl, —CN, —$OR^{7a}$, —$C(O)N(R^{7a})_2$, —$C(O)OR^{7a}$, and —$C(O)R^{7a}$; wherein the $C_{1-6}$ alkyl, $C_{2-6}$ alkenyl, and $C_{2-6}$ alkynyl represented by $R^7$ are each optionally substituted one or more $R^{70}$;

$R^{7a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{7a}$ are each optionally substituted with one or more $R^{70}$;

$R^{70}$, for each occurrence, is independently selected from halogen, —$OR^{70a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$alkyl, $C_{2-6}$alkenyl, $C_{2-6}$alkynyl, 3- to 7-membered monocyclic carbocyclyl and 4- to 6-membered monocyclic heterocyclyl represented by $R^{70}$ are optionally substituted with one or more $R^{75}$;

$R^{70a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{70a}$ are each optionally substituted one or more $R^{75}$;

$R^{75}$, for each occurrence, is independently selected from $C_{1-6}$ alkyl, halogen and —$OR^{75a}$;

$R^{75a}$ is H or $C_{1-6}$ alkyl;

$R^8$, for each occurrence, is independently selected from H, halogen, $C_{1-6}$ alkyl, $C_{2-6}$ alkenyl, $C_{2-6}$ alkynyl, —CN, —$C(O)R^{8a}$, —$C(O)_2R^{8a}$, —$C(O)N(R^{8a})_2$, —$N(R^{8a})_2$, —$N(R^{8a})C(O)R^{8a}$, —$N(R^{8a})C(O)_2R^{8a}$, —$N(R^{8a})C(O)N(R^{8a})_2$, —$N(R^{8a})S(O)_2R^{8a}$, —$OR^{8a}$, —$OC(O)R^{8a}$, —$OC(O)N(R^{8a})_2$, —$SR^{8a}$, —$S(O)R^{8a}$, —$S(O)_2R^{8a}$, —S(O)N($R^{8a}$)$_2$, —S(O)$_2$N($R^{8a}$)$_2$, 3- to 7-membered monocyclic carbocyclyl, 4- to 6-membered monocyclic heterocyclyl, and 7- to 10-membered bicyclic heterocyclyl; wherein the $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl and 7- to 10-membered bicyclic heterocyclyl represented by $R^8$ are each optionally substituted with one or more $R^{80}$;

$R^{8a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{8a}$ are each optionally substituted with one or more $R^{80}$; or two $R^{8a}$, taken together with their intervening atom, form 4- to 6-membered monocyclic heterocyclyl optionally substituted with one or more $R^{80}$;

$R^{80}$, for each occurrence, is independently selected from halogen, $C_{1-6}$ alkyl, $C_{2-6}$ alkenyl, $C_{2-6}$ alkynyl, —CN, —C(O)$R^{80a}$, —C(O)$_2R^{80a}$, —C(O)N($R^{80a}$)$_2$, —N($R^{80a}$)$_2$, —N($R^{80a}$)C(O)$R^{80a}$, —N($R^{80a}$)C(O)$_2$ $R^{80a}$, —N($R^{80a}$)C(O)N($R^{80a}$)$_2$, —N($R^{80a}$)S(O)$_2R^{80a}$, —O$R^{80a}$, —OC(O)$R^{80a}$, —OC(O)N($R^{80a}$)$_2$, —S$R^{80a}$, —S(O)$R^{80a}$, —S(O)$_2R^{80a}$, —S(O)N($R^{80a}$)$_2$, —S(O)$_2$N ($R^{30a}$) 2, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{80}$ are each optionally substituted with one or more $R^{85}$; or two $R^{80}$ together the carbon atom from which they are attached form an oxo group (—C═O)—);

$R^{80a}$, for each occurrence, is independently selected from H, $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl having 1-2 heteroatoms independently selected from O, N and S; wherein the $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl represented by $R^{80a}$ are each optionally substituted with one or more $R^{85}$;

$R^{85}$, for each occurrence, is independently $C_{1-6}$ alkyl, halogen and —O$R^{85a}$; and $R^{85a}$ is H or $C_{1-6}$ alkyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to the subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof for use in treating a disorder responsive to inhibition of Btk.

Other features or advantages will be apparent from the following detailed description of several embodiments, and also from the appended claims.

DETAILED DESCRIPTION

The compounds or pharmaceutically acceptable salts thereof as described herein, can have activity as Btk modulators. In particular, compounds or pharmaceutically acceptable salts thereof as described herein, can be Btk inhibitors.

In a second embodiment, a compound of the present invention is represented by formula (I), or a pharmaceutically acceptable salt thereof, wherein $A^1$ is N, $Q^1$ is C, and $Q^2$ is N; and the definitions for the other variables are as defined in the first embodiment.

In a third embodiment, a compound of the present invention is represented by formula (I), or a pharmaceutically acceptable salt thereof, wherein $A^1$ is CH, $Q^1$ is N, and $Q^2$ is C; and the definitions for the other variables are as defined in the first embodiment.

In a fourth embodiment, a compound of the present invention is represented by formula (I), or a pharmaceutically acceptable salt thereof, wherein $A^1$ is CH; $Q^1$ is C and $Q^2$ is N; and the definitions for the other variables are as defined in the first embodiment.

In a fifth embodiment, a compound of the present invention is represented by any one of the following formulas:

(II)

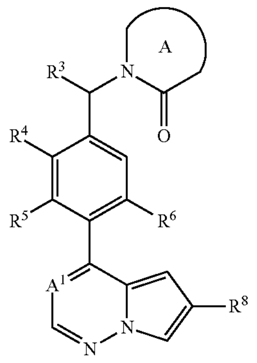

(III)

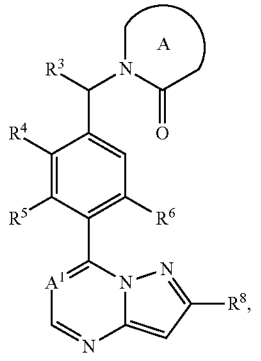

or a pharmaceutically acceptable salt thereof; wherein $A^1$ is N or CH; and the definitions for the other variables are as defined in the first embodiment.

In a sixth embodiment, a compound of the present invention is represented by formula (I), (II), or (III) or a pharmaceutically acceptable salt thereof, wherein Ring A is selected from 5- or 6-membered monocyclic heterocyclyl and 9- or 10-membered bicyclic heterocyclyl, wherein Ring A is optionally substituted with one or two $R^{100}$;

$R^{100}$, for each occurrence, is independently selected from $C_{1-6}$ alkyl, $C_{3-6}$cycloalkyl, 4- to 6-membered monocyclic heterocyclyl, halogen, —CN, —C(O)$R^{100a}$, —C(O)$_2R^{100a}$; —C(O)N($R^{100a}$)$_2$, —N($R^{100a}$)$_2$, —N($R^{100a}$)C(O)$R^{100a}$, —N($R^{100a}$)C(O)$_2R^{100a}$, —N($R^{100a}$)C(O)N($R^{100a}$)$_2$, —N($R^{100a}$)S(O)$_2R^{100a}$, —O$R^{100a}$, —OC(O)$R^{100a}$, —OC(O)N($R^{100a}$)$_2$, —$SR^{100a}$, —$S(O)R^{100a}$, —$S(O)_2R^{100a}$, —$S(O)N(R^{100a})_2$, and —$S(O)_2N(R^{100a})_2$, wherein the $C_{1-6}$ alkyl, $C_{3-6}$cycloalkyl, 4- to 6-membered monocyclic heterocyclyl represented by $R^{100}$ are each optionally substituted with one to three $R^{150}$; or two $R^{100}$ taken together with their intervening atom, form 4- to 6-membered monocyclic heterocyclyl or 3- to 7-membered monocyclic carbocyclyl, each or which is optionally substituted with one ore more $R^{150}$; and $R^{100a}$, for each occurrence, is independently selected from H, $C_{1-6}$ alkyl, $C_{3-6}$cycloalkyl, and 4- to 6-membered monocyclic heterocyclyl; and $R^{150}$ is $R^{150}$, for each occurrence, is independently selected from $C_{1-6}$ alkyl, halogen and —$OR^{150a}$;

$R^{150a}$ is H or $C_{1-6}$ alkyl$^0$; and the definitions for the other variables are as defined in the first, second, third, fourth or fifth embodiment.

In a seventh embodiment, a compound of the present invention is represented by formula (I), (II), or (III) or a pharmaceutically acceptable salt thereof, wherein wherein Ring A is represented by one of following formula:

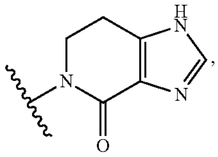
,
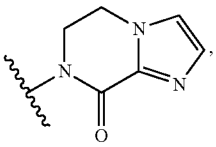
,
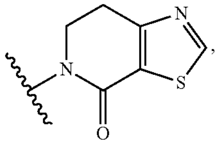
,
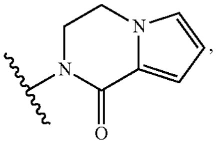
,
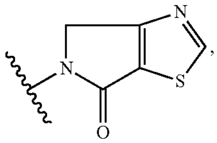
,
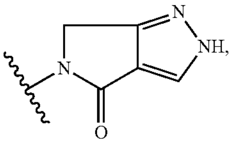
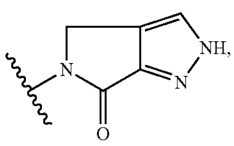
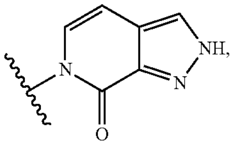
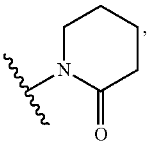
,
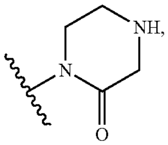
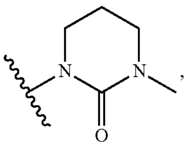
,
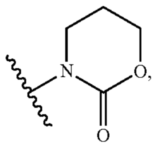
,
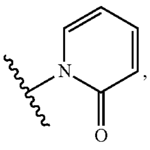
,
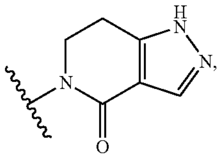
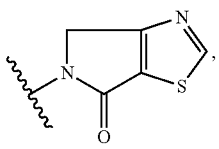
, -continued

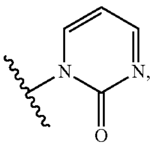
or
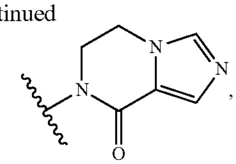
, wherein any one of which is optionally substituted with one or two $R^{100}$; and the definitions for the other variables are as defined in the first, second, third, fourth, fifth or sixth embodiment.

In an eighth embodiment, a compound of the present invention is represented by formula (I), (II), or (III) or a pharmaceutically acceptable salt thereof, wherein Ring A is represented by one of following formulae:

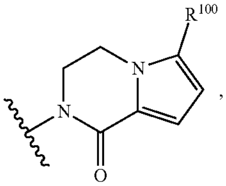
,
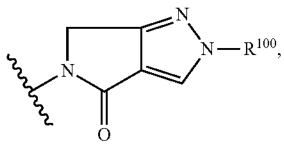
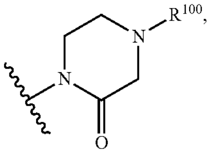
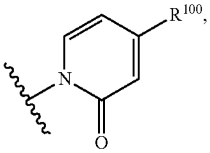
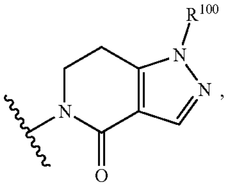
,
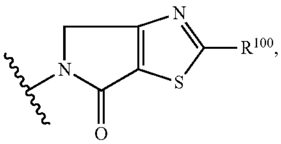
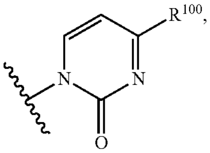
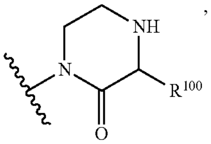
,
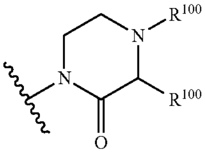
or
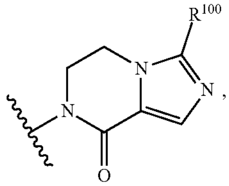
, wherein any one of which is optionally substituted with one or two $R^{100}$; and the definitions for the other variables are as defined in the first, second, third, fourth, fifth, sixth or seventh embodiment.

In a ninth embodiment, a compound of the present invention is represented by formula (I), (II), or (III), or a pharmaceutically acceptable salt thereof, wherein:

$R^{100}$, for each occurrence, is independently selected from $C_{1-6}$ alkyl, $C_{3-6}$ cycloalkyl, halogen, —CN, and —$OR^{100a}$; wherein the $C_{1-6}$ alkyl and $C_{3-6}$cycloalkyl are each optionally substituted with one to three substituents independently selected from halogen and $C_{1-3}$alkyl;

$R^{100a}$, for each occurrence, is independently selected from H, $C_{1-6}$ alkyl, $C_{3-6}$cycloalkyl, and 4- to 6-membered monocyclic heterocyclyl; and the definitions for the other variables are as defined in the first, second, third, fourth, fifth, sixth, seventh or eighth embodiment.

In a tenth embodiment, a compound of the present invention is represented by formula (I), (II), or (III), or a pharmaceutically acceptable salt thereof, wherein $R^{100}$, for each occurrence, is independently $C_{1-6}$alkyl or $C_{3-6}$cycloalkyl, wherein the $C_{1-6}$alkyl and $C_{3-6}$cycloalky are each optionally substituted with one to three halo; and the definitions for the other variables are as defined in the first, second, third, fourth, fifth, sixth, seventh, eighth or ninth embodiment.

In an eleventh embodiment, a compound of the present invention is represented by formula (I), (II), or (III), or a pharmaceutically acceptable salt thereof, wherein $R^{100}$ is $—C(CH_3)_3$, $—CH_2C(CH_3)_3$ or 3,3-difluorocyclobutyl; and the definitions for the other variables are as defined in the first, second, third, fourth, fifth, sixth, seventh, eighth or ninth embodiment.

In a twelfth embodiment, a compound of the present invention is represented by formula (I), (II), or (III), or a pharmaceutically acceptable salt thereof, wherein $R^3$ is H; and the definitions for the other variables are as defined in the first, second, third, fourth, fifth, sixth, seventh, eighth, ninth, tenth, or eleventh embodiment.

In a thirteenth embodiment, a compound of the present invention is represented by formula (I), (II), or (III), or a pharmaceutically acceptable salt thereof, wherein:

$R^4$ is selected from halogen, —CN, $—OR^{4a}$, $C_{1-6}$ alkyl, and $C_{3-6}$ cycloalkyl, wherein the $C_{1-6}$ alkyl and $C_{3-6}$cycloalkyl represented by $R^4$ are each optionally substituted with 1-3 halogen; and $R^{4a}$ is $C_{1-4}$alkyl optionally substituted with one to three halogen; and the definitions for the other variables are as defined in the first, second, third, fourth, fifth, sixth, seventh, eighth, ninth, tenth, eleventh, or twelfth embodiment.

In a fourteenth embodiment, a compound of the present invention is represented by formula (I), (II), or (III), or a pharmaceutically acceptable salt thereof, wherein $R^4$ is selected from $—CH_3$, $—CF_3$, $—CHF_2$, $—CH_2CHF_2$, and cyclopropyl; and the definitions for the other variables are as defined in the first, second, third, fourth, fifth, sixth, seventh, eighth, ninth, tenth, eleventh, twelfth or thirteenth embodiment.

In a fifteenth embodiment, a compound of the present invention is represented by formula (I), (II), or (III), or a pharmaceutically acceptable salt thereof, wherein $R^4$ is $—CH_3$; and the definitions for the other variables are as defined in the first, second, third, fourth, fifth, sixth, seventh, eighth, ninth, tenth, eleventh, twelfth, or thirteenth embodiment.

In a sixteenth embodiment, a compound of the present invention is represented by formula (I), (II), or (III), or a pharmaceutically acceptable salt thereof, wherein $R^5$ is H or halogen; and the definitions for the other variables are as defined in the first, second, third, fourth, fifth, sixth, seventh, eighth, ninth, tenth, eleventh twelfth, thirteenth, fourteenth, or fifteenth embodiment.

In a seventeenth embodiment, a compound of the present invention is represented by formula (I), (II), or (III), or a pharmaceutically acceptable salt thereof, wherein $R^5$ is H or F; and the definitions for the other variables are as defined in the first, second, third, fourth, fifth, sixth, seventh, eighth, ninth, tenth, eleventh twelfth, thirteenth, fourteenth, fifteenth or sixteenth embodiment.

In an eighteenth embodiment of the present invention, the compound is represented by formula (I), (II), (III), or a pharmaceutically acceptable salt thereof, wherein $R^5$ is H; and the definitions for the other variables are as defined in the first, second, third, fourth, fifth, sixth, seventh, eighth, ninth, tenth, eleventh twelfth, thirteenth, fourteenth, fifteenth or sixteenth embodiment.

In a nineteenth embodiment, a compound of the present invention is represented by formula (I), (II), or (III), or a pharmaceutically acceptable salt thereof, wherein $R^6$ is H or halogen; and the definitions for the variables are as defined in the first, second, third, fourth, fifth, sixth, seventh, eighth, ninth, tenth, eleventh, twelfth, thirteenth fourteenth, fifteenth, sixteenth, seventeenth, or eighteenth embodiment.

In a twentieth embodiment, a compound of the present invention is represented by formula (I), (II), or (III), or a pharmaceutically acceptable salt thereof, wherein $R^6$ is H or F; and the definitions for the variables are as defined in the first, second, third, fourth, fifth, sixth, seventh, eighth, ninth, tenth, eleventh, twelfth, thirteenth fourteenth, fifteenth, sixteenth, seventeenth, or eighteenth embodiment.

In a twenty-first embodiment, a compound of the present invention is represented by formula (I), (II), (III), or a pharmaceutically acceptable salt thereof, wherein $R^6$ is H or F; and the definitions for the variables are as defined in the first, second, third, fourth, fifth, sixth, seventh, eighth, ninth, tenth, eleventh, twelfth, thirteenth fourteenth, fifteenth, sixteenth, seventeenth, or eighteenth embodiment.

In a twenty-second embodiment, a compound of the present invention is represented by formula (I), (II), (III), or a pharmaceutically acceptable salt thereof, wherein:

$R^8$, for each occurrence, is independently selected from H, halogen, $C_{2-6}$ alkynyl, $—C(O)R^{8a}$, $—C(O)N(R^{8a})_2$, $—N(R^{8a})_2$, $—OR^{8a}$, —CN, $C_{1-6}$ alkyl, $C_{2-6}$ alkenyl, phenyl, $C_{3-6}$ cycloalkyl, 4- to 6-membered monocyclic heterocyclyl having 1-2 heteroatoms independently selected from O, N and S, and 7- to 10-membered bicyclic heterocyclyl having 1-4 heteroatoms independently selected from O, N and S; wherein the $C_{1-6}$ alkyl, $C_{2-6}$ alkenyl, $C_{2-6}$ alkynyl, phenyl, $C_{3-6}$ cycloalkyl, 4- to 6-membered monocyclic heterocyclyl, and 7- to 10-membered bicyclic heterocyclyl represented by $R^8$ are each optionally substituted with one to three $R^{80}$;

$R^{8a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{8a}$ are each optionally substituted with one or three $R^{80}$; or two $R^{8a}$, taken together with their intervening atom, form 4- to 6-membered monocyclic heterocyclyl optionally substituted with one to three $R^{80}$;

$R^{80}$, for each occurrence, is independently selected from halogen, —CN, $—C(O)R^{80a}$, $—OR^{80a}$, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{80}$ are each optionally substituted with one or three $R^{85}$; or two $R^{80}$ together the carbon atom from which they are attached form an oxo group (—C═O)—); and $R^{80a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl having 1-2 heteroatoms independently selected from O, N and S;

$R^{85}$, for each occurrence, is independently selected from halogen and $—OR^{85a}$;

$R^{85a}$ is H or $C_{1-6}$ alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, or twenty-first embodiment.

In a twenty-third embodiment, a compound of the present invention is represented by formula (I), (II), or (III), or a pharmaceutically acceptable salt thereof, wherein:

$R^8$, for each occurrence, is independently selected from H, halogen, $C_{1-6}$ alkyl, $C_{2-6}$ alkynyl, —C(O)$R^{8a}$, —C(O)N($R^{8a}$)$_2$, —N($R^{8a}$)$_2$, —O$R^{8a}$, —CN, phenyl, 4- to 6-membered monocyclic heterocyclyl having 1-2 heteroatoms independently selected from O, N and S, and 7- to 10-membered bicyclic heterocyclyl having 1-3 heteroatoms independently selected from O, N and S; wherein the $C_{1-6}$ alkyl, $C_{2-6}$ alkynyl, phenyl, 4- to 6-membered monocyclic heterocyclyl, and 7- to 10-membered bicyclic heterocyclyl represented by $R^8$ are each optionally substituted with one to three $R^{80}$;

$R^{8a}$, for each occurrence, is independently selected from $C_{1-6}$ alkyl and 4- to 6-membered monocyclic heterocyclyl, wherein the $C_{1-6}$ alkyl and 4- to 6-membered monocyclic heterocyclyl represented by $R^{8a}$ are each optionally substituted with one to three $R^{80}$;

$R^{80}$, for each occurrence, is independently selected from halogen, —CN, —C(O)$R^{80a}$, —O$R^{80a}$, $C_{1-6}$ alkyl, $C_{3-6}$ cycloalkyl, and 4- to 6-membered monocyclic heterocyclyl, wherein the $C_{1-6}$ alkyl, $C_{3-6}$cycloalkyl, and 4- to 6-membered monocyclic heterocyclyl represented by $R^{80}$ are each optionally substituted with one to three $R^{85}$; or two $R^{80}$ together the carbon atom from which they are attached form an oxo group (—C═O)—);

$R^{80a}$, for each occurrence, is independently selected from H, $C_{1-6}$ alkyl and $C_{2-6}$ alkenyl;

$R^{85}$, for each occurrence, is independently selected from halogen and —O$R^{85a}$; and $R^{85a}$ is H or $C_{1-3}$alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, or twenty-first embodiment.

In a twenty-fourth embodiment, a compound of the present invention is represented by formula (I), (II), or (III), or a pharmaceutically acceptable salt thereof, wherein:

$R^8$ is selected from H, F, Br, —CN, —$OC_2H_5OCH_3$, —N($CH_3$)($CH_2CH_2OCH_3$), —C(O)N($CH_3$)$_2$,

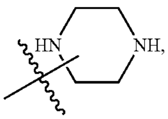 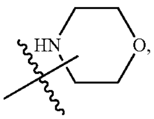 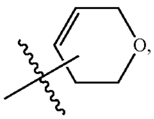

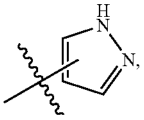 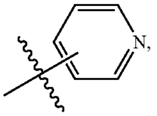 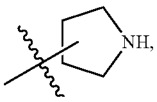

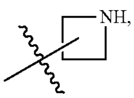 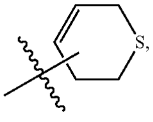 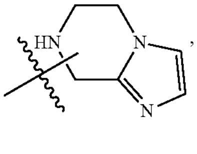 ,

-continued

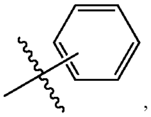 , 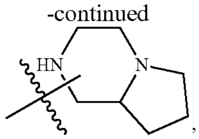 , 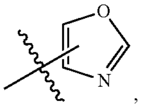 ,

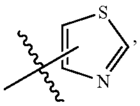 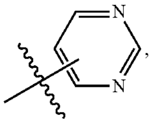 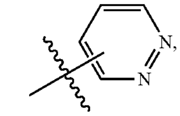

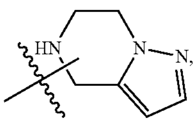 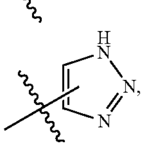 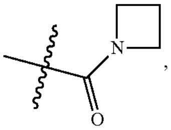 ,

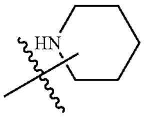 , 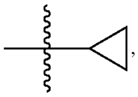 , 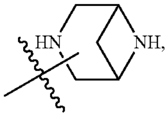

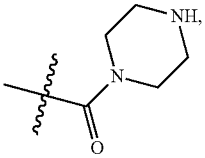 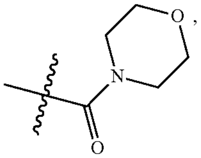

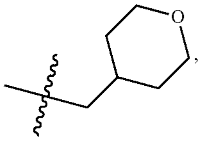 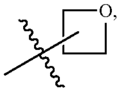 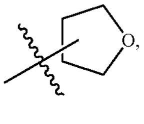 and

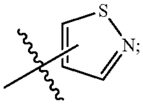

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second or twenty-third embodiment.

In a twenty-fifth embodiment, a compound of the present invention is represented by formula (I), (II), or (III), or a pharmaceutically acceptable salt thereof, wherein:

$R^{80}$ is selected from halogen, —CN, —C(O)$R^{80a}$, —O$R^{80a}$, $C_{1-3}$ alkyl, $C_{3-6}$ cycloalkyl, and 4- to 6-membered monocyclic heterocyclyl having 1-2 heteroatoms selected from O and N; wherein the $C_{1-3}$ alkyl, $C_{3-6}$ cycloalkyl, and 4- to 6-membered monocyclic heterocyclyl represented by $R^{80}$ are each optionally substituted with one to three $R^{85}$; or two $R^{80}$ together with the carbon atom from which they are attached from an oxo (—C(═O)) group;

$R^{80a}$, for each occurrence, is independently selected from $C_{1-4}$alkyl and $C_{2-4}$ alkenyl; and $R^{85}$, for each occurrence, is independently selected from F, —OH or $C_{1-3}$alkoxy; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third or twenty-fourth embodiment.

In a twenty-sixth embodiment, a compound of the present invention is represented by formula (I), (II), or (III), or a pharmaceutically acceptable salt thereof, wherein $R^{80}$, for each occurrence, is independently selected from —F, —$CH_3$, —$CHF_2$, —$CH_2OH$, —$C_2H_5$, —$CH_2CHF_2$, —CN, —$OCH_3$, —C(O)($CH_2C{=}CH$), —C(O)($CH{=}CCH_3$), —$CH_2CH_2OCH_3$,

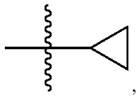

, and

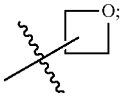

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third, twenty-fourth or twenty-fifth embodiment.

In a twenty-seventh embodiment, a compound of the present invention is represented by formula (I), (II), or (III), or a pharmaceutically acceptable salt thereof, wherein $R^8$ is selected from H, —$OCH_2CH_2OCH_3$, —C(O)N($CH_3$)$_2$, and

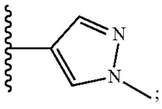

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth or twenty-first embodiment.

In a twenty-eighth embodiment, a compound of the present invention is represented by any one of the following formulas:

(IIA)

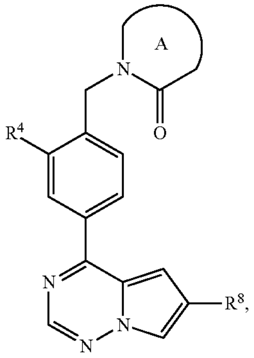

-continued (IIB)

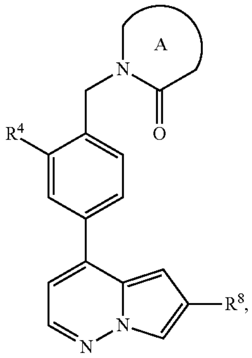

(IIIA)

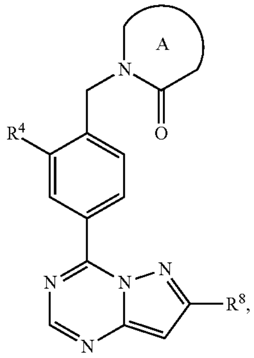

(IIIB)

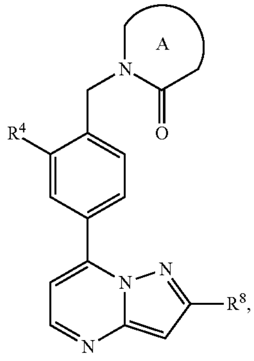

(IIIC)

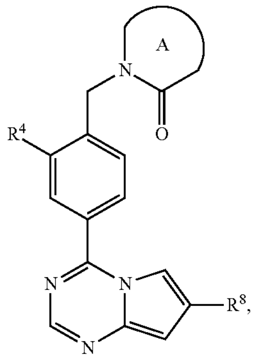

-continued (IID)

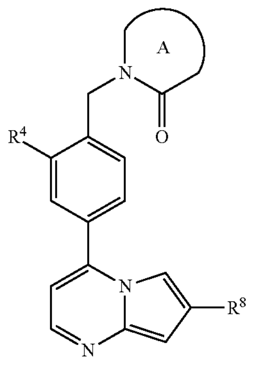

or a pharmaceutically acceptable salt thereof, wherein:

Ring A is selected from 5- or 6-membered monocyclic heterocyclyl and 9- or 10-membered bicyclic heterocyclyl; wherein Ring A is optionally substituted with one or two $R^{100}$;

$R^{100}$ is $C_{1-6}$alkyl or $C_{4-6}$cycloalkyl, wherein $C_{1-6}$alkyl and $C_{4-6}$cycloalky are each optionally substituted with one to three halo;

$R^4$ is $C_{1-4}$alkyl optionally substituted with one to three halo;

$R^8$, for each occurrence, is independently selected from H, halogen, $C_{1-6}$ alkyl, —C(O)N($R^{8a}$)$_2$, —O$R^{8a}$, 5- or 6-membered monocyclic heteroaryl having 1-2 heteroatoms independently selected from O, N and S; wherein the $C_{1-6}$ alkyl and 5- or 6-membered monocyclic heteroaryl represented by $R^8$ are each optionally substituted with one to three $R^{80}$;

$R^{8a}$, for each occurrence, is independently $C_{1-6}$alkyl optionally substituted with one to three $R^{80}$;

$R^{80}$, for each occurrence, is independently selected from $C_{1-4}$alkyl, halogen and —O$R^{80a}$; and $R^{80a}$, for each occurrence, is independently selected from H or $C_{1-3}$ alkyl; and the definitions for the other variables are as defined in the first embodiment.

In a twenty-ninth embodiment, a compound of the present invention is represented by formula (IIA), (IIB), (IIIA), (IIIB), (IIIC), or (IIID), or a pharmaceutically acceptable salt thereof, wherein Ring A is represented by one of the follow formulae:

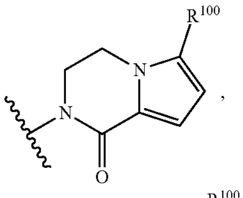
,
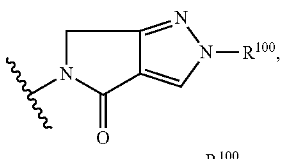
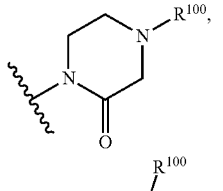
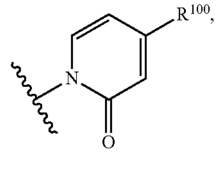
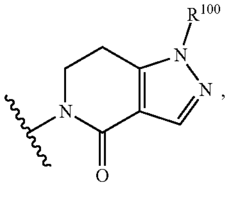
,
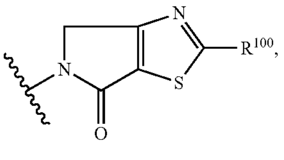

-continued

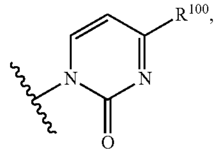
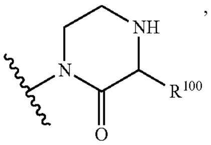
,
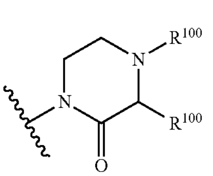
or
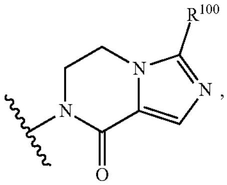
, wherein any one of which is optionally substituted with one or two independently selected $R^{100}$;

$R^{100}$, for each occurrence, is independently $C_{1-6}$alkyl or $C_{4-6}$cycloalkyl, wherein the $C_{1-6}$alkyl and $C_{4-6}$cycloalky are each optionally substituted with one to three halo; and the definitions for the other variables are as defined in the first or twenty-eighth embodiment.

In a thirtieth embodiment, a compound of the present invention is represented by formula (IIA), (IIB), (IIIA), (IIIB), (IIIC), or (IIID), or a pharmaceutically acceptable salt thereof, wherein $R^8$, for each occurrence, is independently selected from H, —C(O)N($R^{8a}$)$_2$, —O$R^{8a}$, and 5-membered monocyclic heteroaryl having 1-2 heteroatoms independently selected from O, N and S; wherein the $C_{1-6}$ alkyl and 5- or 6-membered monocyclic heteroaryl represented by $R^8$ are each optionally substituted with one to three $R^{80}$;

$R^{8a}$, for each occurrence, is independently $C_{1-6}$alkyl optionally substituted with one to three $R^{80}$;

$R^{80}$, for each occurrence, is independently selected from $C_{1-4}$alkyl, halogen and —O$R_{80a}$; and $R^{80a}$, for each occurrence, is independently selected from H or $C_{1-3}$ alkyl; and the definitions for the other variables are as defined in the first, twenty-eighth, or twenty-ninth embodiment.

In a thirty-first embodiment, a compound of the present invention is represented by formula (IIA), (IIB), (IIIA), (IIIB), (IIIC), or (IIID), or a pharmaceutically acceptable salt thereof, wherein $R^4$ is —$CH_3$; and the definitions for the other variables are as defined in the first, twenty-eighth, twenty-ninth or thirtieth embodiment.

In a thirty-second embodiment, a compound of the present invention is represented by formula (IIA), (IIB), (IIIA), (IIIB), (IIIC), or (IIID), or a pharmaceutically acceptable salt thereof, wherein $R^8$ is H, —$OCH_2CH_2OCH_3$, —C(O)N($CH_3$)$_2$, and

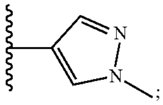 [SMILES: *c1cnn(C)c1]
;

and the definitions for the other variables are as defined in the first, twenty-eighth, twenty-ninth, or thirty-first embodiment.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 10-ring members, or in particular 3- to 8-ring members, 3- to 7-ring members, 3- to 6-ring members or 5- to 7-ring members, 4- to 7-ring members or 4- to 6-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings.

In one embodiment, a heterocyclyl is a 3- to 7-membered monocyclic heterocyclyl (saturated or partially unsaturated (i.e., non-aromatic)) having 1-2 heteroatoms selected from O, S and N. Examples of 3- to 7-membered monocyclic heterocyclyl include, but are not limited to, aziridinyl, oxiranyl, thirranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl. In one embodiment, a heterocyclyl is a 5- to 7-membered monocyclic heterocyclyl (saturated or partially unsaturated).

In one embodiment, a heterocyclyl is a 4- to 6-membered monocyclic heterocyclyl (saturated or partially unsaturated) having 1-2 heteroatoms selected from O, S and N. Examples of a 4- to 6-membered monocyclic heterocyclic include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl having 1-2 heteroatoms selected from O, S and N. Examples of saturated 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is oxetanyl, tetrahydrofuranyl, or tetrahydropyranyl.

In one embodiment, a 4- to 6-membered monocyclic heterocyclyl is selected from

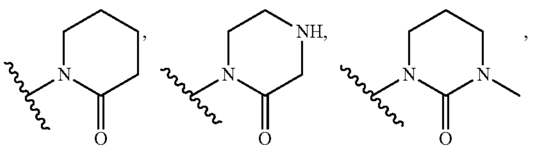

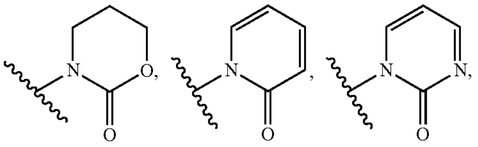

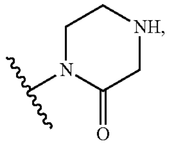

and

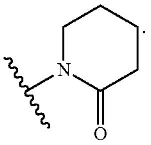

In another embodiment, a 4- to 6-membered monocyclic heterocyclyl is selected from

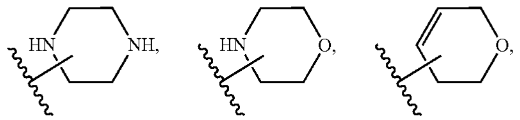

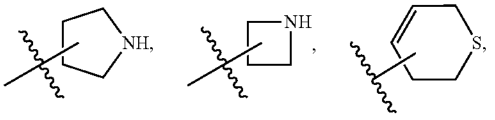

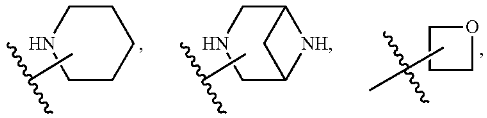

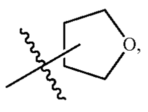

and

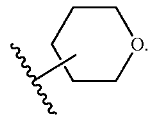

In one embodiment, a heterocyclyl is a 7-membered monocyclic heterocyclyl (saturated or partially unsaturated), such as a 7-membered monocyclic heterocyclyl having one heteroatom selected from O and N. Examples of a 7-membered monocyclic heterocyclyl include, but are not limited to, azepanyl, azepinyl, oxepanyl, oxepinyl, thiepanyl, thiepinyl, diazepanyl, diazepinyl, and thiazepinyl.

In another embodiment, a heterocyclyl is a 7- to 10-membered bicyclic heterocyclyl. In yet another embodiment, a heterocyclyl is a 9- to 10-membered non-aromatic bicyclic heterocyclyl. In another embodiment, a heterocyclyl is 9- to 10-membered fused non-aromatic bicyclic heterocyclyl. The heterocyclyl group can be attached to the rest of a compound of the invention at a heteroatom or a carbon atom. In one embodiment, a 9- to 10-membered fused non-aromatic bicyclic heterocyclyl is selected from

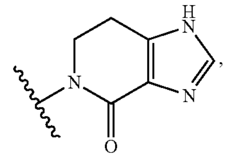,
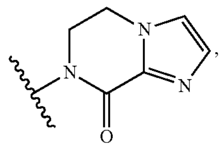,
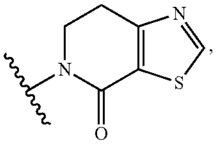,
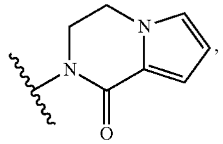,
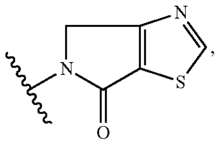,
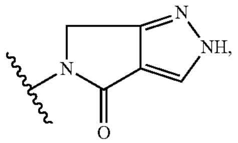
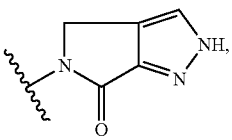
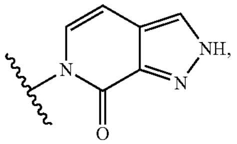
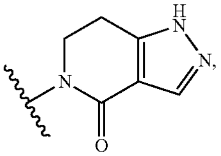
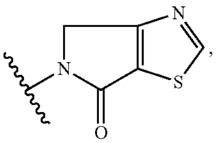, and
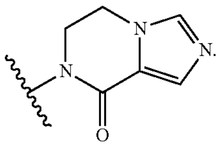

In another embodiment, a heterocyclyl is a 7- to 8-membered bridged non-aromatic bicyclic heterocyclyl, such as

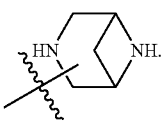

As used herein, the term "heteroaryl" refers to an aromatic 5- to 6-membered monocyclic ring system, having 1 to 4 heteroatoms independently selected from O, N and S, and wherein N can be oxidized (e.g., N(O)) or quaternized, and S can be optionally oxidized to sulfoxide and sulfone. Examples of 5- to 6-membered monocyclic heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, and the like. In one embodiment, a heteroaryl is a 5-membered heteroaryl. Examples of a 5-membered heteroaryl include, but are not limited to, pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl. In one embodiment, a 5-membered heteroaryl is selected from

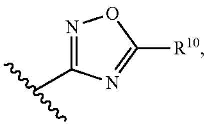
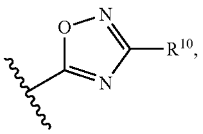
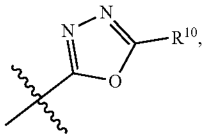
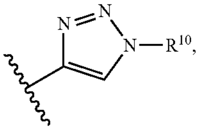
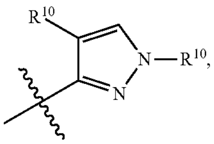
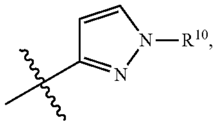
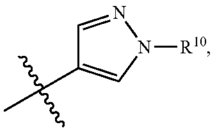
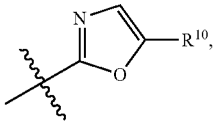
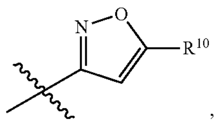,
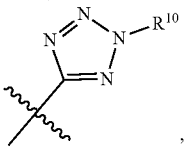,
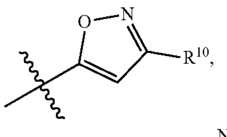
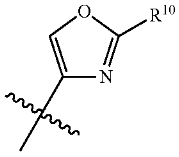 and
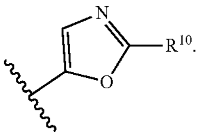

The term "fused ring system", as used herein, is a ring system that has two rings each of which are independently selected from a carbocyclyl or a heterocyclyl, wherein the two ring structures share two adjacent ring atoms. In one embodiment, a fused ring system have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, and S. In one embodiment, a bridged ring system have from 6 to 8 ring members.

The term "spiro ring system," as used herein, is a ring system that has two rings each of which are independently selected from a carbocyclyl or a heterocyclyl, wherein the two ring structures having one ring atom in common. In one embodiment, spiro ring systems have from 5 to 8 ring members.

As used herein, the term "carbocyclyl" refers to saturated or unsaturated monocyclic or bicyclic hydrocarbon groups of 3-7 carbon atoms, 3-5, 3-6, 4-6, or 5-7 carbon atoms. The term "carbocyclyl" encompasses cycloalkyl groups and aromatic groups (i.e., aryl). The term "cycloalkyl" refers to completely saturated monocyclic or bicyclic or spiro hydrocarbon groups of 3-7 carbon atoms, 3-6 carbon atoms, or 5-7 carbon atoms. Exemplary bicyclic carbocyclyl groups include bicyclo[2.1.1]hexyl, bicyclo[2.2.1]heptyl, bicyclo [2.2.1]heptenyl, tricyclo[2.2.1.0$^{2,6}$]heptanyl, 6,6-dimethyl-bicyclo[3.1.1]heptyl, or 2,6,6-trimethylbicyclo[3.1.1]heptyl, spiro[2.2]pentanyl, and spiro[3.3]heptanyl.

In one embodiment, the carbocyclyl is a 3- to 7-membered monocyclic carbocyclyl. Exemplary 3- to 7-membered monocyclic carbocyclyls include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. In one embodiment, the carbocyclyl is a 5- to 7-membered monocyclic carbocyclyl. In another embodiment, the carbocyclyl is a 4- to 6-membered monocyclic carbocyclyl, such as but not limited to cycloheptyl. In another embodiment, the carbocyclyl is a 4- to 6-membered monocyclic carbocyclyl. In another embodiment, the carbocyclyl is a 3- to 6-membered carbocyclyl. In another embodiment, the carbocyclyl is a 3- to 6-membered cycloalkyl. In yet another embodiment, the carbocyclyl is phenyl. In yet another embodiment, the carbocyclyl is cyclopropyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the invention provides deuterated compounds disclosed herein, in which any or more positions occupied by hydrogen can include enrichment by deuterium above the natural abundance of deuterium. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to the subject an effective amount of at least one compound described herein, or a pharmaceutically acceptable salt thereof.

In one embodiment, the present invention provides methods of treating autoimmune disorders, inflammatory disorders, and cancers in a subject in need thereof comprising administering to the subject an effective amount of at least one compound described herein, or a pharmaceutically acceptable salt thereof.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenia purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis. In some embodiments, the present invention provides a method of treating systemic lupus erythematosus or atopic dermatitis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 μg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

Abbreviations and acronyms used herein include the following:

AcOH means acetic acid;
$(BPin)_2$ means bis(pinacolato)diboron;
$CH_3CN$ means acetonitrile;
$CD_3OD$ means deutero-methanol
δ means chemical shift;
d means doublet;
dd means double doublet;
DCM means dichloromethane;
EtOAc means ethyl acetate;
HCl means hydrochloric acid;
$^1H$ NMR means proton nuclear magnetic resonance;
$H_2O$ means water;
HPLC means high pressure liquid chromatography;
$K_2CO_3$ means potassium carbonate;
KOAc means potassium acetate;
m means multiplet;
Me means methyl;
MeOH means methanol;
mg means milligram;
MHz means mega Hertz;
mins means minutes;
mL means millilitres;
mmol means millimole;
MS m/z means mass spectrum peak;
$N_2$ means nitrogen;
$NaBH(OAc)_3$ means sodium triacetoxyborohydride;
$NaBH_4$ means sodium borohydride;

NatBuO means sodium tert-butoxide;
$Na_2CO_3$ means sodium carbonate;
NaH means sodium hydride;
$NaHCO_3$ means sodium bicarbonate;
NaI means sodium iodide;
NaOH means sodium hydroxide;
$Na_2SO_3$ means sodium thiosulfate;
$Na_2SO_4$ means sodium sulfate;
$Pd(dppf)Cl_2$ means [1,1'-bis(diphenylphosphino)ferrocene]dichloropalladium(II);
$Pd(dppf)Cl_2{\cdot}DCM$ means [1,1'-bis(diphenylphosphino) ferrocene]dichloropalladium(II), complex with dichloromethane;
Pd means palladium;
$Pd(PPh_3)_2Cl_2$ means Dichlorobis(triphenylphosphine) palladium(II);
q means quartet;
RT means room temperature;
s means singlet;
t means triplet;
t-BuONa means sodium tert-butoxide;
TFA means trifluoroacetic acid;
XPhos means 2-Dicyclohexylphosphino-2',4',6'-triisopropylbiphenyl
XPhos Pd G3 means a third generation (G3) Buchwald precatalyst Example 1:3-methyl-1-(2-methyl-4-(pyrrolo[2,1-f][1,2,4]triazin-4-yl)benzyl)piperazin-2-one (compound 1)

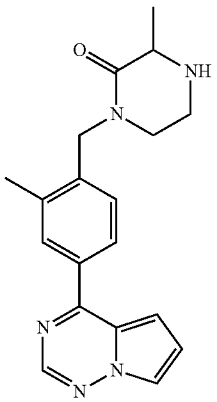 [SMILES: Cc1cc(-c2ncnn3cccc23)ccc1CN1CCNC(C)C1=O]

1. Synthesis of tert-butyl 4-(4-bromo-2-methylbenzyl)-2-methyl-3-oxopiperazine-1-carboxylate

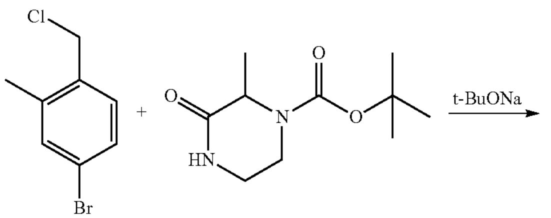

-continued

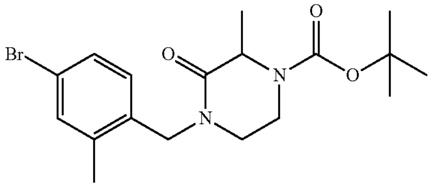

A solution of 4-bromo-1-(chloromethyl)-2-methyl-benzene (1.0 g, 4.7 mmol), tert-butyl 2-methyl-3-oxo-piperazine-1-carboxylate (1.0 g, 4.7 mmol) and sodium tert-butoxide (1.4 g, 14 mmol) in dioxane (5 mL) was heated to reflux overnight. The cooled reaction mixture was diluted with EtOAc (15 mL) and washed sequentially with water (20 mL) and brine (20 mL). The washed organic phase was dried ($Na_2SO_4$) and concentrated in vacuo. The crude material was purified by silica gel column chromatography (0-100% EtOAc/Heptanes) to give tert-butyl 4-(4-bromo-2-methylbenzyl)-2-methyl-3-oxopiperazine-1-carboxylate (1.1 g, yield: 58%). ESI-MS $(M+H)^+$: 397.1.

2. Synthesis of tert-butyl 2-methyl-4-(2-methyl-4-(4,4,5,5-tetramethyl-1,3,2-dioxaborolan-2-yl)benzyl)-3-oxopiperazine-1-carboxylate

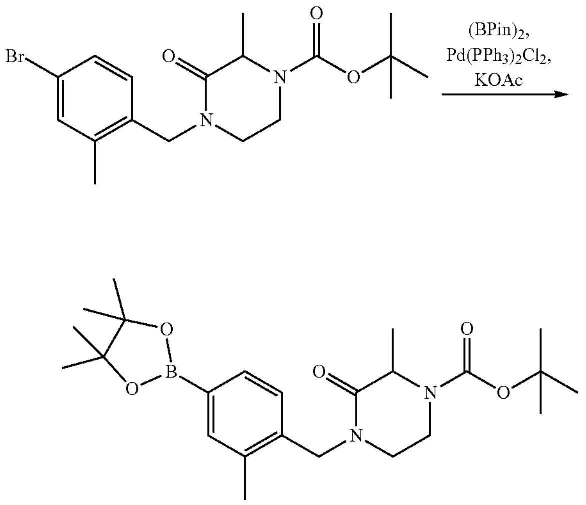

A solution of tert-butyl 4-(4-bromo-2-methylbenzyl)-2-methyl-3-oxopiperazine-1-carboxylate (1.1 g, 2.7 mmol), (bispinacolato)diboron (690 mg, 2.7 mmol), bis(triphenylphosphine)palladium chloride (191 mg, 0.27 mmol) and potassium acetate (803 mg, 8.2 mmol) in dioxane (6 mL) was heated to reflux overnight. The cooled reaction mixture was diluted with EtOAc (15 mL) and filtered through Celite®. The filtrate was concentrated in vacuo the residue was purified by silica gel column chromatography (0-100% EtOAc/Heptanes) to give tert-butyl 2-methyl-4-(2-methyl-4-(4,4,5,5-tetramethyl-1,3,2-dioxaborolan-2-yl)benzyl)-3-oxopiperazine-1-carboxylate (1.1 g, yield: 86%). ESI-MS (M+H−t-Bu−pinacol)$^+$: 307.0.

3. Synthesis of tert-butyl 2-methyl-4-(2-methyl-4-(pyrrolo[2,1-f][1,2,4]triazin-4-yl)benzyl)-3-oxopiperazine-1-carboxylate

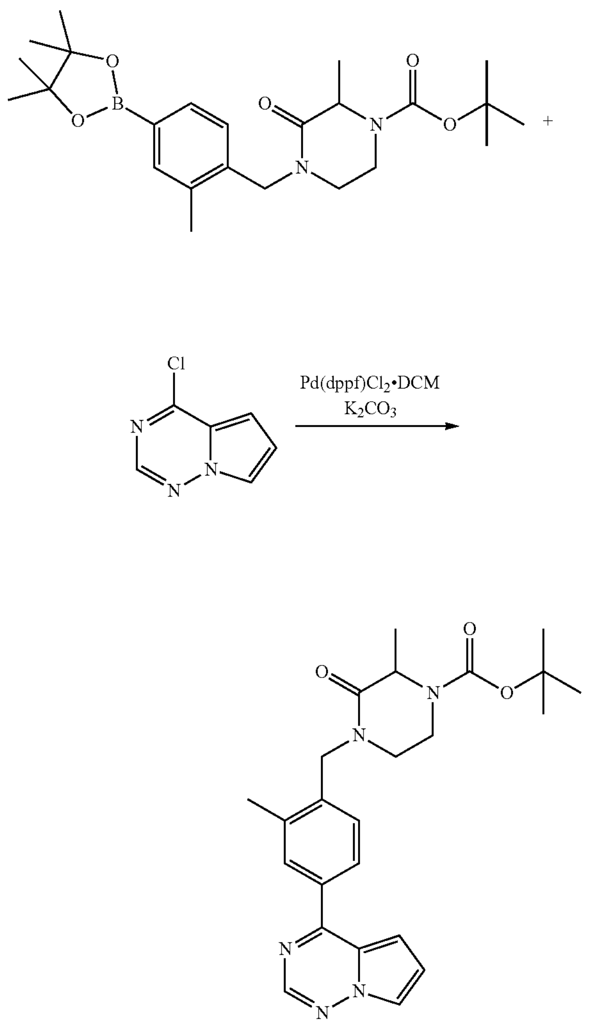

A solution of tert-butyl 2-methyl-4-(2-methyl-4-(4,4,5,5-tetramethyl-1,3,2-dioxaborolan-2-yl)benzyl)-3-oxopiperazine-1-carboxylate (444 mg, 1.0 mmol), 4-chloropyrrolo[2,1-f][1,2,4]triazine (154 mg, 1.0 mmol), potassium carbonate (415 mg, 3.0 mmol), and Pd(dppf)$Cl_2$·DCM (93 mg, 0.1 mmol) in dioxane (2 mL) and water (0.2 mL) was heated to 95° C. for 16 h. The cooled reaction mixture was diluted with EtOAc (10 mL) and filtered through Celite®. The filtrate was concentrated in vacuo the residue was purified by silica gel column chromatography (0-20% MeOH/DCM) to give tert-butyl 2-methyl-4-(2-methyl-4-(pyrrolo[2,1-f][1,2,4]triazin-4-yl)benzyl)-3-oxopiperazine-1-carboxylate (393 mg, yield: 90%). ESI-MS $(M+H)^+$: 436.2.

4. Synthesis of 3-methyl-1-(2-methyl-4-(pyrrolo[2,1-f][1,2,4]triazin-4-yl)benzyl)piperazin-2-one (Example BM-1)

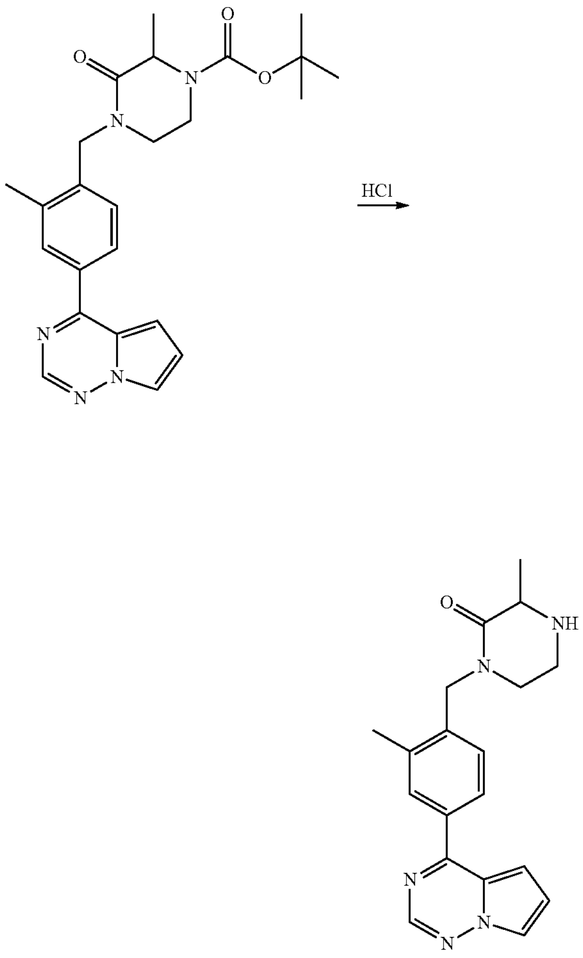

To a solution of tert-butyl 2-methyl-4-(2-methyl-4-(pyrrolo[2,1-f][1,2,4]triazin-4-yl)benzyl)-3-oxopiperazine-1-carboxylate (393 mg, 0.90 mmol) in MeOH (2 mL) was added an HCl solution (0.9 mL, 4 M in dioxane). The reaction mixture was stirred at ambient temperature overnight. The crude material was concentrated in vacuo and carried forward. A small amount was purified by prep-HPLC ($CH_3CN/H_2O$ with 0.05% TFA/$H_2O$ as mobile phase) to give the TFA salt of 3-methyl-1-(2-methyl-4-(pyrrolo[2,1-f][1,2,4]triazin-4-yl)benzyl)piperazin-2-one (14 mg). ESI-MS $(M+H)^+$: 336.1. $^1H$ NMR (400 MHZ, $CD_3OD$) δ: 8.78-8.65 (m, 1H), 8.63-8.45 (m, 1H), 8.06-7.86 (m, 2H), 7.83-7.72 (m, 1H), 7.68-7.56 (m, 1H), 7.51-7.32 (m, 1H), 4.81-4.46 (m, 2H), 4.37-4.06 (m, 1H), 3.92-3.41 (m, 4H), 2.51 (br s, 3H), 1.80-1.50 (m, 3H).

Example 2: Synthesis of 4-isobutyl-3-methyl-1-(2-methyl-4-(pyrrolo[2,1-f][1,2,4]triazin-4-yl)benzyl)piperazin-2-one (compound 2)

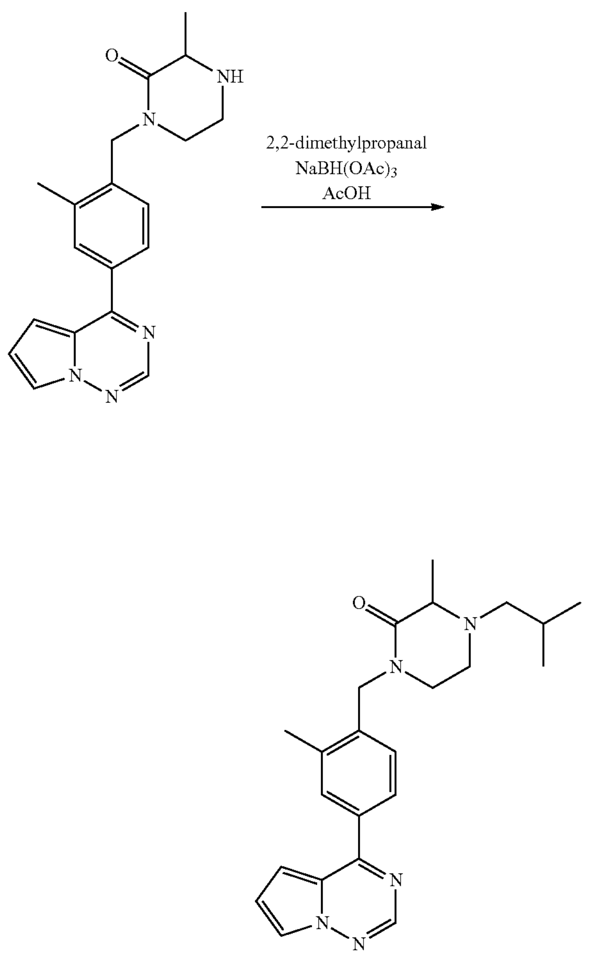

To a solution of 3-methyl-1-(2-methyl-4-(pyrrolo[2,1-f][1,2,4]triazin-4-yl)benzyl)piperazin-2-one (262 mg, 0.78 mmol), 2,2-dimethylpropanal (135 mg, 1.56 mmol), and acetic acid (47 mg, 0.78 mmol) in DCM (2 mL) was added sodium triacetoxyborohydride (331 mg, 1.56 mmol). The reaction mixture was stirred at ambient temperature overnight. The reaction mixture was quenched with MeOH and the crude solution was directly purified by prep-HPLC ($CH_3CN/H_2O$ with 0.05% TFA/$H_2O$ as mobile phase) to give the TFA salt of 4-isobutyl-3-methyl-1-(2-methyl-4-(pyrrolo[2,1-f][1,2,4]triazin-4-yl)benzyl)piperazin-2-one (45 mg, yield: 11%). ESI-MS $(M+H)^+$: 392.2. $^1H$ NMR (400 MHZ, $CD_3OD$) δ: 8.48 (s, 1H), 8.13-8.03 (m, 1H), 7.98-7.87 (m, 2H), 7.45 (d, J=7.8 Hz, 1H), 7.25-7.17 (m, 1H), 7.12 (dd, J=4.6 Hz, 2.6 Hz, 1H), 4.97-4.90 (m, 1H), 4.73 (d, J=15.6 Hz, 1H), 4.28-4.13 (m, 1H), 3.93-3.78 (m, 1H), 3.72-3.52 (m, 3H), 3.30-3.19 (m, 1H), 3.12 (dd, J=13.1 Hz, 6.0 Hz, 1H), 2.46 (s, 3H), 2.27-2.09 (m, 1H), 1.75 (d, J=7.3 Hz, 3H), 1.10 (t, J=6.9 Hz, 6H).

Example 3: Synthesis of 4-(3,3-difluorocyclobutyl)-3-methyl-1-(2-methyl-4-(pyrrolo[2,1-f][1,2,4]triazin-4-yl)benzyl)piperazin-2-one (compound 3)

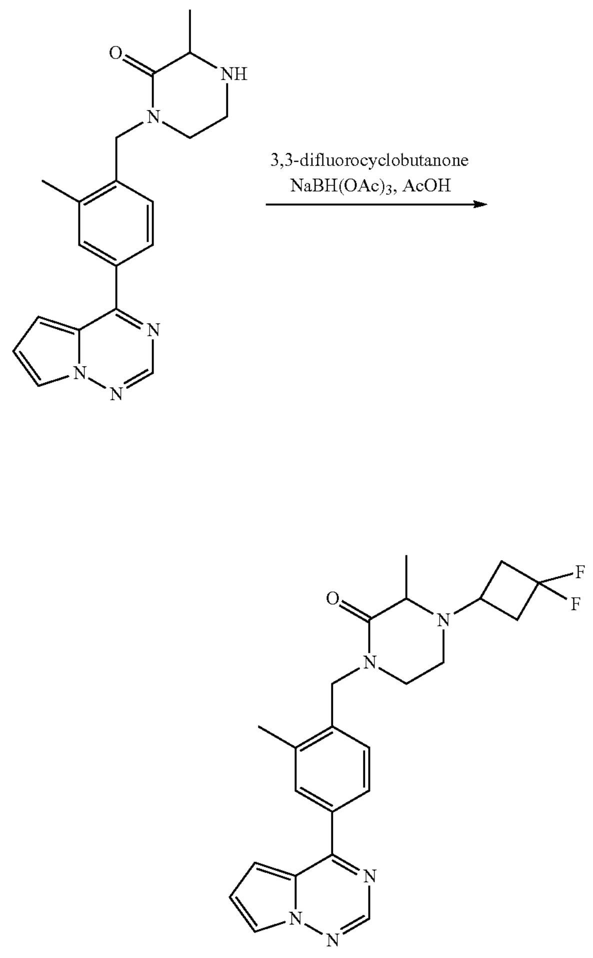 [SMILES: Cc1cc(-c2ncnn3cccc23)ccc1CN1CCNC(C)C1=O ; "3,3-difluorocyclobutanoneNaBH(OAc)3, AcOH" ; Cc1cc(-c2ncnn3cccc23)ccc1CN1CCN(C2CC(F)(F)C2)C(C)C1=O]

To a solution of 3-methyl-1-(2-methyl-4-(pyrrolo[2,1-f][1,2,4]triazin-4-yl)benzyl)piperazin-2-one (655 mg, 1.95 mmol), 3,3-difluorocyclobutanone (414 mg, 3.90 mmol), and acetic acid (117 mg, 1.95 mmol) in DCM (2 mL) was added sodium triacetoxyborohydride (827 mg, 3.90 mmol). The reaction mixture was stirred at ambient temperature overnight. The reaction mixture was quenched with MeOH and the crude solution was directly purified by prep-HPLC ($CH_3CN/H_2O$ with 0.05% TFA/$H_2O$ as mobile phase) to give 4-(3,3-difluorocyclobutyl)-3-methyl-1-(2-methyl-4-(pyrrolo[2,1-f][1,2,4]triazin-4-yl)benzyl)piperazin-2-one (4 mg, yield: 1%). ESI-MS $(M+H)^+$: 426.2. $^1H$ NMR (400 MHZ, $CD_3OD$) δ: 8.49 (s, 1H), 8.10 (s, 1H), 7.97-7.90 (m, 2H), 7.42 (t, J=7.0 Hz, 1H), 7.26 (t, J=4.6 Hz, 1H), 7.14 (dd, J=4.6 Hz, 2.6 Hz, 1H), 5.01-4.89 (m, 2H), 4.79-4.61 (m, 2H), 4.47 (br d, J=7.5 Hz, 1H), 3.90-3.80 (m, 1H), 3.70-3.59 (m, 1H), 3.45-3.34 (m, 2H), 3.18-3.06 (m, 1H), 3.01-2.85 (m, 1H), 2.83-2.66 (m, 1H), 2.46 (s, 3H), 1.69-1.49 (m, 3H).

Example 4:4-isobutyl-3-methyl-1-(2-methyl-4-(6-(1-methyl-1H-pyrazol-4-yl)pyrrolo[2,1-f][1,2,4]triazin-4-yl)benzyl)piperazin-2-one (compound 4)

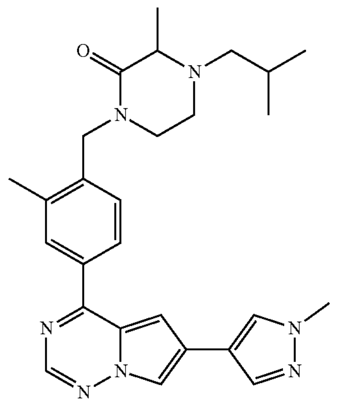

1. Synthesis of tert-butyl 4-(4-(6-bromopyrrolo[2,1-f][1,2,4]triazin-4-yl)-2-methylbenzyl)-2-methyl-3-oxopiperazine-1-carboxylate

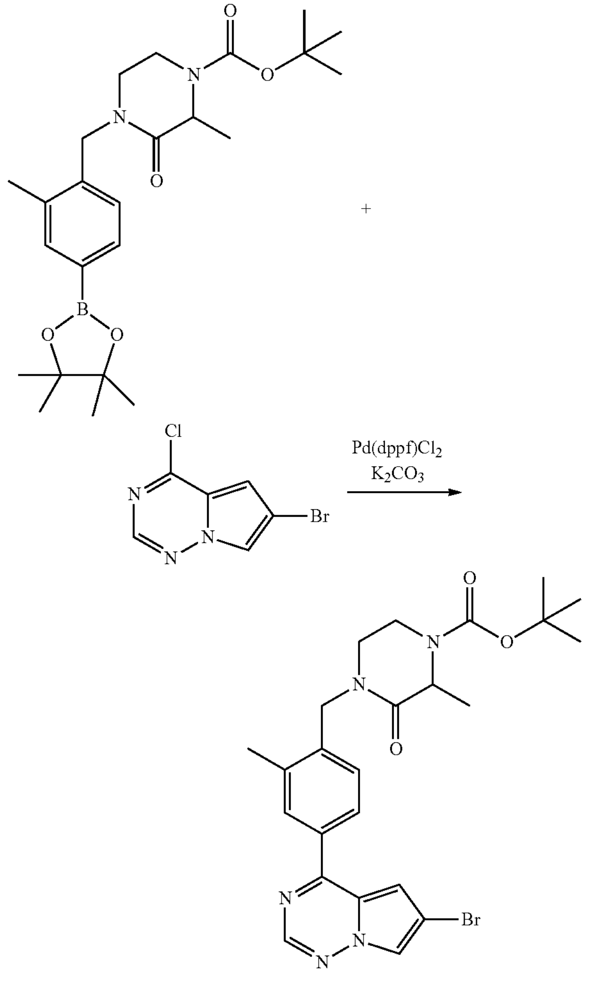

A solution of tert-butyl 2-methyl-4-(2-methyl-4-(4,4,5,5-tetramethyl-1,3,2-dioxaborolan-2-yl)benzyl)-3-oxopiperazine-1-carboxylate (191 mg, 0.43 mmol), 6-bromo-4-chloro-pyrrolo[2,1-f][1,2,4]triazine (200 mg, 0.86 mmol), Pd(dppf)$Cl_2$ (31 mg, 0.043 mmol) and potassium carbonate (178 mg, 1.29 mmol) in dioxane (2 mL) and water (0.2 mL) was degassed with $N_2$ and heated to 95° C. for 16 h. The cooled reaction mixture was diluted with EtOAc (10 mL) and filtered through Celite®. The filtrate was concentrated in vacuo the residue was purified by silica gel column chromatography (0-100% EtOAc/Heptanes) to give tert-butyl 4-(4-(6-bromopyrrolo[2,1-f][1,2,4]triazin-4-yl)-2-methylbenzyl)-2-methyl-3-oxopiperazine-1-carboxylate (96 mg, yield: 43%). ESI-MS $(M+H)^+$: 514.0.

2. Synthesis of tert-butyl 2-methyl-4-(2-methyl-4-(6-(1-methyl-1H-pyrazol-4-yl)pyrrolo[2,1-f][1,2,4]triazin-4-yl)benzyl)-3-oxopiperazine-1-carboxylate

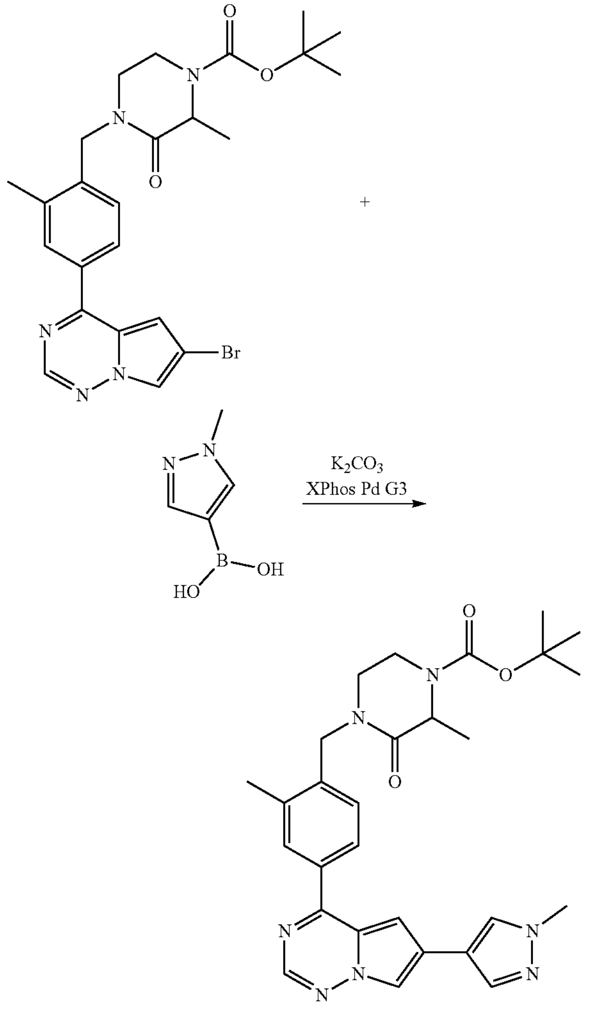

A solution of tert-butyl 4-(4-(6-bromopyrrolo[2,1-f][1,2,4]triazin-4-yl)-2-methylbenzyl)-2-methyl-3-oxopiperazine-1-carboxylate (52 mg, 0.11 mmol), (1-methylpyrazol-4-yl) boronic acid (38 mg, 0.31 mmol), potassium carbonate (42 mg, 0.31 mmol) and XPhos Pd G3 (9 mg, 0.01 mmol) in dioxane (2 mL) and water (0.2 mL) was degassed with $N_2$ and heated to 95° C. overnight. The cooled reaction mixture was diluted with EtOAc (10 mL) and filtered through Celite®. The filtrate was concentrated in vacuo the residue was purified by silica gel column chromatography (0-100% EtOAc/Heptanes) to give tert-butyl 2-methyl-4-(2-methyl-4-(6-(1-methyl-1H-pyrazol-4-yl)pyrrolo[2,1-f][1,2,4]triazin-4-yl)benzyl)-3-oxopiperazine-1-carboxylate (12 mg, yield: 23%). 1H NMR (400 MHZ, $CDCl_3$) δ: 85.1-8.47 (m, 1H), 8.05-8.00 (m, 1H), 7.96-7.90 (m, 2H), 7.79-7.76 (m, 1H), 7.68-7.65 (m, 1H), 7.33-7.28 (m, 1H), 7.13-7.08 (m, 1H), 5.00-4.88 (m, 1H), 4.78-4.65 (m, 1H), 4.62-4.50 (m, 1H), 4.10-4.03 (m, 1H), 3.99-3.92 (m, 3H), 3.46-3.34 (m, 1H), 3.31-3.18 (m, 1H), 3.16-3.06 (m, 1H), 2.47-2.41 (m, 3H), 1.55-1.51 (m, 3H), 1.49 (s, 9H).

3. Synthesis of 3-methyl-1-(2-methyl-4-(6-(1-methyl-1H-pyrazol-4-yl)pyrrolo[2,1-f][1,2,4]triazin-4-yl)benzyl)piperazin-2-one

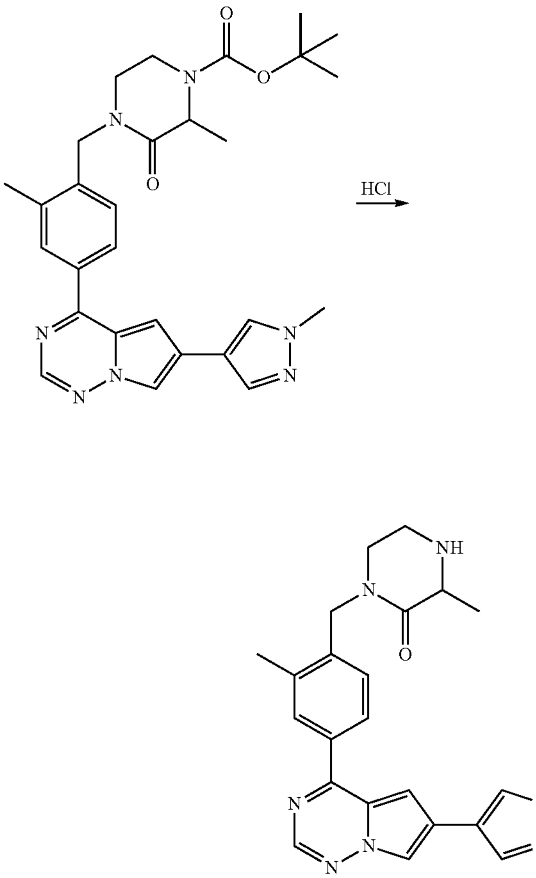

To a solution of tert-butyl 2-methyl-4-(2-methyl-4-(6-(1-methyl-1H-pyrazol-4-yl)pyrrolo[2,1-f][1,2,4]triazin-4-yl)benzyl)-3-oxopiperazine-1-carboxylate (12 mg, 0.02 mmol) in MeOH (2 mL) was added an HCl solution (23 μL, 4 M in dioxane). The reaction mixture was stirred at ambient temperature overnight. The reaction mixture was concentrated in vacuo and crude 3-methyl-1-(2-methyl-4-(6-(1-methyl-1H-pyrazol-4-yl)pyrrolo[2,1-f][1,2,4]triazin-4-yl)benzyl)piperazin-2-one (11 mg, crude) was carried forward without further purification. ESI-MS $(M+H)^+$: 416.3.

4. Synthesis of 4-isobutyl-3-methyl-1-(2-methyl-4-(6-(1-methyl-1H-pyrazol-4-yl)pyrrolo[2,1-f][1,2,4]triazin-4-yl)benzyl)piperazin-2-one (Example BM-4)

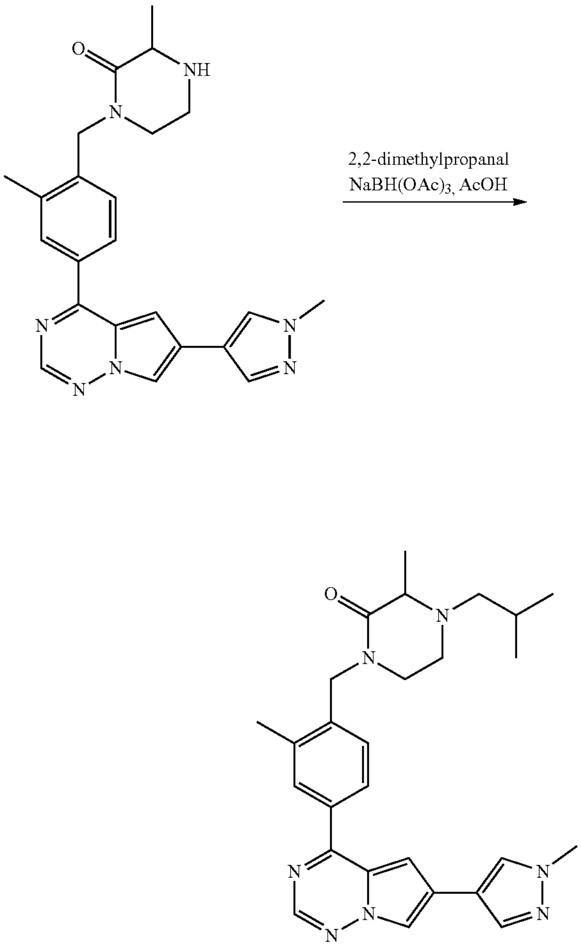

To a solution of 3-methyl-1-(2-methyl-4-(6-(1-methyl-1H-pyrazol-4-yl)pyrrolo[2,1-f][1,2,4]triazin-4-yl)benzyl)piperazin-2-one (11 mg, 0.027 mmol) in DCM (2 mL) was added 2,2-dimethylpropanal (4.6 mg, 0.054 mmol), and acetic acid (1.6 mg, 0.027 mmol), followed by sodium triacetoxyborohydride (11 mg, 0.054 mmol). The reaction mixture was stirred at ambient temperature overnight. The reaction mixture was quenched with MeOH and the crude solution was directly purified by prep-HPLC ($CH_3CN/H_2O$ with 0.05% $TFA/H_2O$ as mobile phase) to give 4-isobutyl-3-methyl-1-(2-methyl-4-(6-(1-methyl-1H-pyrazol-4-yl)pyrrolo[2,1-f][1,2,4]triazin-4-yl)benzyl)piperazin-2-one (5 mg, yield: 35%). ESI-MS $(M+H)^+$: 472.3. $^1H$ NMR (500 MHZ, $CDCl_3$) δ: 8.59 (s, 1H), 8.27 (br s, 1H), 7.96-7.88 (m, 3H), 7.80 (s, 1H), 7.48 (d, J=7.6 Hz, 1H), 7.40 (br s, 1H), 4.87 (br d, J=15.3 Hz, 1H), 4.74 (d, J=15.3 Hz, 1H), 4.07-4.04 (m, 1H), 4.02 (s, 3H), 3.63 (br d, J=11.0 Hz, 2H), 3.44 (br s, 2H), 3.12 (br d, J=7.3 Hz, 1H), 2.94 (dd, J=12.8 Hz, 5.5 Hz, 1H), 2.45 (s, 3H), 2.22 (br d, J=5.5 Hz, 1H), 1.85 (br s, 3H), 1.19 (d, J=6.7 Hz, 3H), 1.13 (d, J=6.7 Hz, 3H).

Using methods and procedures similar to those described in Examples 1-4, the following compounds can be prepared.

TABLE 1
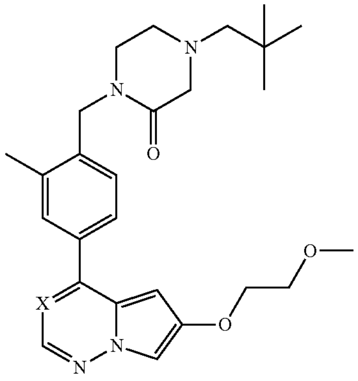
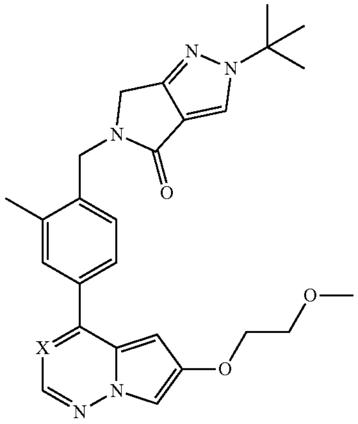
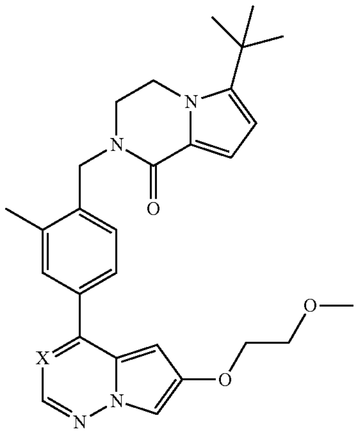
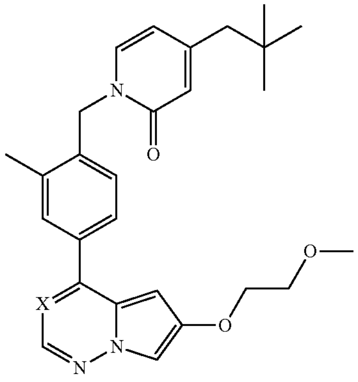
TABLE 1-continued
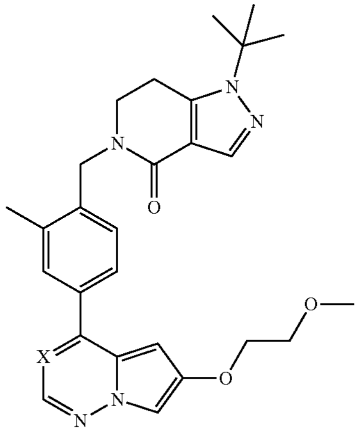
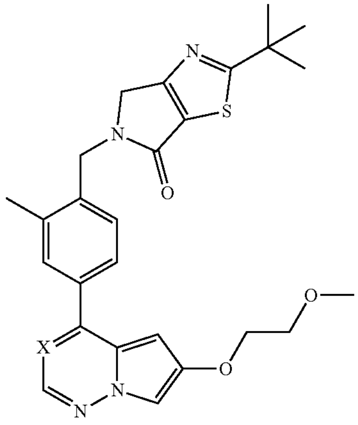
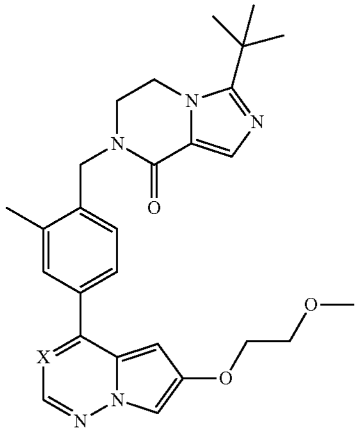

TABLE 1-continued
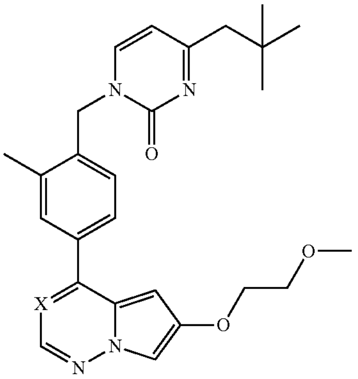
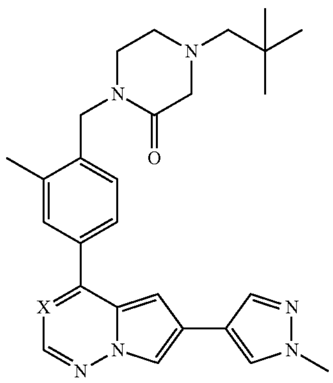
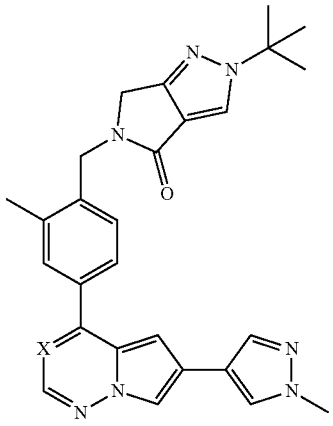
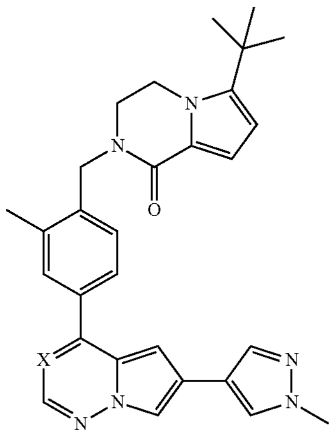
TABLE 1-continued
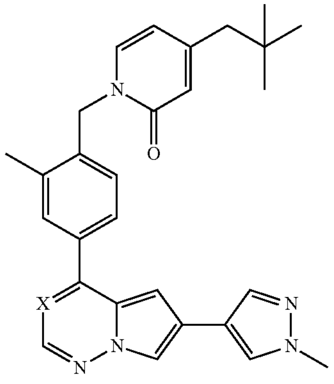
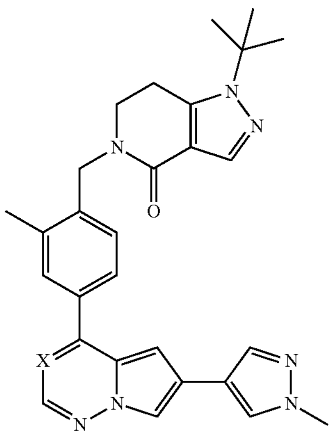
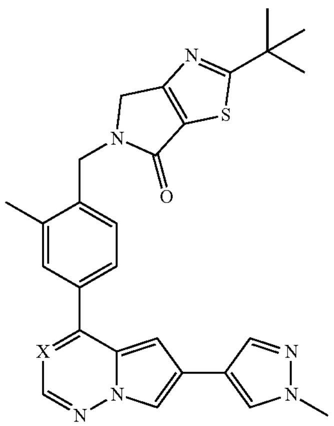

TABLE 1-continued
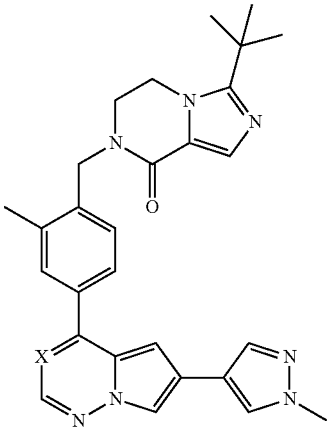
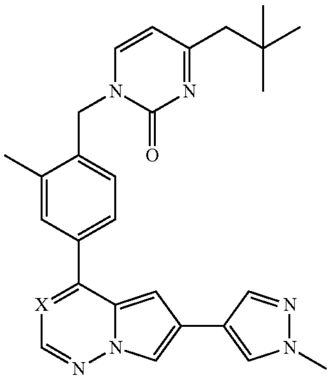
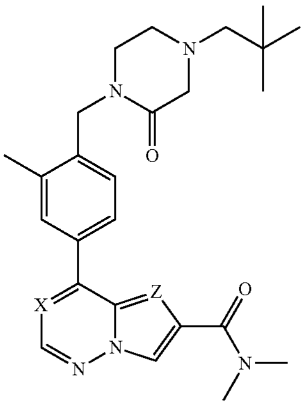
TABLE 1-continued
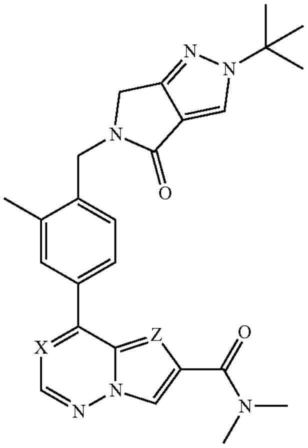
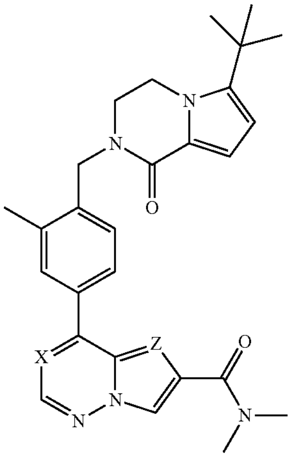
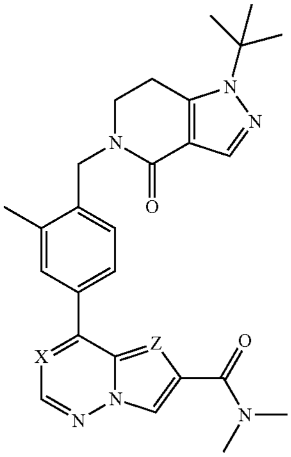

TABLE 1-continued

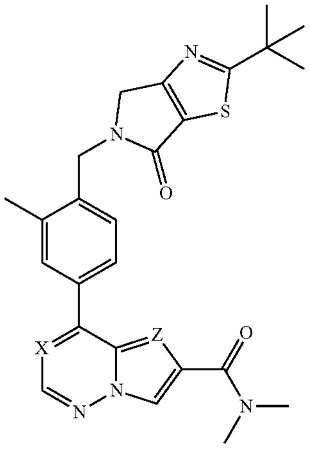

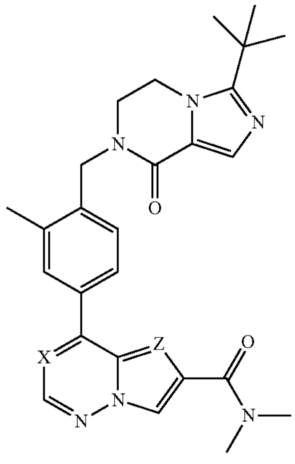

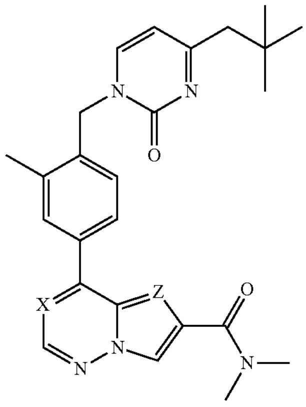

X = N or CH; and Z = N or CH

In Vitro BTK Kinase Assay: Btk-PolyGAT-LS Assay

The purpose of the BTK in vitro assay is to determine compound potency against BTK through the measurement of $IC_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 pL aliquot of a ATP/peptide master mix (final concentration; ATP 10 μM, polyGAT 100 nM) in kinase buffer (10 mM Tris-HCl pH 7.5, 10 mM MgC12, 200 μM $Na_3PO_4$, 5 mM DTT, 0.01% Triton X-100, and 0.2 mg/ml casein) is added to each well. Next, I pL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 pL of a 50 mM EDTA solution. Aliquots (5 uL) of the kinase reaction are transferred to a low volume white 384 well plate (Coming 3674), and 5 pL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. $IC_{50}$ values are calculated using a four parameter fit with 100% enzyme activity determined from the DMSO control and 0% activity from the EDTA control.

Table 2 shows the activity of the selected exemplary compounds of this invention in the in vitro Btk kinase assay, wherein each compound number corresponds to the compound numbering set forth in the Examples 1-4 herein. "†" represents an $IC_{50}$ of greater than 1 μM and equal to or less than 10 μM. "††" represents an $IC_{50}$ of greater than 10 nM and equal to or less than 1 μM (10 nM<$IC_{50}$≤1 μM). "†††" represents an $IC_{50}$ of greater than 1 nM and equal to or less than 10 nM (1 nM<$IC_{50}$≤10 nM).

TABLE 2

| Compound No. | $IC_{50}$ (nM) |
|---|---|
| 1, 3 | † |
| 2 | †† |
| 4 | ††† |

In Vitro whole blood CD69 Assay

Human heparinized venous blood from health donors was aliquoted into 96-well plate and "spiked" with serial dilutions of formula I compounds in DMSO or with DMSO without drug. The final concentration of DMSO in all wells was 0.1%. The plate was incubated at 37° C. for 30 min. Drug-containing samples were stimulated with 0.1 μg/mL mouse anti-human IgD-dextran ($1A^{62}$) or 20 μg/mL polyclonal rabbit F(ab')2 anti-human IgD. Phosphate-buffered saline (PBS) was added to the negative control unstimulated sample and the plates were incubated overnight (18 to 22 hours) at 37° C. Cells were stained with fluorochrome-conjugated anti-CD19 and anti-CD69 antibodies. Lyse/fix solution was used to remove red blood cells by hypotonic lysis and to fix the remaining cells, which were then analyzed by flow cytometry. CD19+ B cells were gated and analyzed for CD69 expression. The percentage of B cells expressing CD69 was plotted versus the log 10 of the concentration of the drug and the best-fit curves (variable Hill slope) were generated to obtain the IC50 value.

Compounds 1, 2, and 4 were tested and all have an $IC_{50}$≥10 μM.

What is claimed is:

1. A compound represented by Formula (I):

(I)

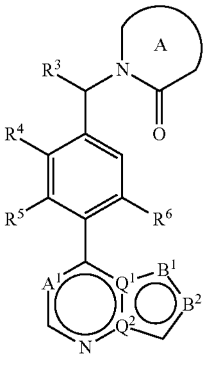

or a pharmaceutically acceptable salt thereof, wherein:

Ring A is a monocyclic 3- to 7-membered heterocyclyl or bicyclic 7- to 10-membered heterocyclyl, wherein Ring A is optionally substituted with one or more independently selected $R^{100}$ substituents;

each $R^{100}$ is independently halogen, CN, $C_{1-6}$ alkyl, $C_{2-6}$ alkenyl, $C_{2-6}$ alkynyl, $C(O)R^{100a}$, $C(O)NR^{100a}R^{100a}$, $C(O)OR^{100a}$, $NR^{100a}R^{100a}$, $NR^{100a}C(O)R^{100a}$, $NR^{100a}C(O)NR^{100a}R^{100a}$, $NR^{100a}C(O)OR^{100a}$, $NR^{100a}S(O)_2R^{100a}$, $OR^{100a}$, $OC(O)R^{100a}$, $OC(O)NR^{100a}R^{100a}$, $SR^{100a}$, $S(O)R^{100a}$, $S(O)NR^{100a}R^{100a}$, $S(O)_2R^{100a}$, $S(O)_2NR^{100a}R^{100a}$, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{150}$ substituents; or any two $R^{100}$, taken together with their intervening atom(s), independently form a monocyclic 3- to 7-membered carbocyclyl or monocyclic 4- to 6-membered heterocyclyl, wherein each 3- to 7-membered carbocyclyl and 4- to 6-membered heterocyclyl is optionally and independently substituted with one or more independently selected $R^{150}$ substituents;

each $R^{100a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{150}$ substituents;

each $R^{150}$ is independently halogen, $C_{1-6}$ alkyl, or $OR^{150a}$;

each $R^{150a}$ is independently H or $C_{1-6}$ alkyl;

$R^3$ is H, $C_{1-6}$ alkyl, $C_{2-6}$ alkenyl, $C_{2-6}$ alkynyl, $C(O)R^{3a}$, $C(O)NR^{3a}R^{3a}$, or $C(O)OR^{3a}$, wherein the $C_{1-6}$ alkyl, $C_{2-6}$ alkenyl, or $C_2$-6 alkynyl is optionally substituted with one or more independently selected $R^{30}$ substituents;

each $R^{3a}$ is independently H, $C_{1-6}$ alkyl, $C_{2-6}$ alkenyl, or $C_2$-6 alkynyl, wherein each $C_{1-6}$ alkyl, $C_{2-6}$ alkenyl, and $C_{2-6}$ alkynyl is optionally and independently substituted with one or more independently selected $R^{30}$ substituents;

each $R^{30}$ is independently halogen, $C_{1-6}$ alkyl, $C_{2-6}$ alkenyl, $C_{2-6}$ alkynyl, $OR^{30a}$, monocyclic 3- to 7-membered carbocyclyl, or monocyclic 4- to 6-membered heterocyclyl;

each $R^{30a}$ is independently H, $C_{1-6}$ alkyl, $C_{2-6}$ alkenyl, $C_{2-6}$ alkynyl, monocyclic 3- to 6-membered carbocyclyl, or monocyclic 4- to 6-membered heterocyclyl;

$R^4$ is H, halogen, CN, $NO_2$, $C_{1-6}$ alkyl, $C_{2-6}$ alkenyl, $C_{2-6}$ alkynyl, $C(O)R^{4a}$, $C(O)NR^{4a}R^{4a}$, $C(O)OR^{4a}$, $NR^{4a}R^{4a}$, $NR^{4a}C(O)R^{4a}$, $NR^{4a}C(O)OR^{4a}$, $NR^{4a}S(O)_2R^{4a}$, $OR^{4a}$, $OC(O)R^{4a}$, $OC(O)NR^{4a}R^{4a}$, $SR^{4a}$, $S(O)R^{4a}$, $S(O)_2R^{4a}$, $S(O)_2NR^{4a}R^{4a}$, monocyclic 3- to 7-membered carbocyclyl, or monocyclic 4- to 6-membered heterocyclyl, wherein the $C_{1-6}$ alkyl, $C_{2-6}$ alkenyl, $C_{2-6}$ alkynyl, 3- to 7-membered carbocyclyl, or 4- to 6-membered heterocyclyl is optionally substituted with one or more independently selected $R^{40}$ substituents;

each $R^{4a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{40}$ substituents;

each $R^{40}$ is independently halogen, $C_{1-6}$ alkyl, $C_{2-6}$ alkenyl, $C_{2-6}$ alkynyl, $OR^{40a}$, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{45}$ substituents;

each $R^{40a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{45}$ substituents;

each $R^{45}$ is independently halogen, $C_{1-6}$ alkyl, or $OR^{45a}$;

each $R^{45a}$ is independently H or $C_{1-6}$ alkyl; or $R^3$ and $R^4$, taken together with their intervening atoms, form Ring B;

Ring B is a monocyclic 5- to 7-membered carbocyclyl or monocyclic 5- to 7-membered heterocyclyl;

wherein the 5- to 7-membered heterocyclyl contains 1 or 2 heteroatoms independently selected from the group consisting of N, O, and S; and wherein Ring B is optionally substituted with one or more independently selected $R^{300}$ substituents;

each $R^{300}$ is independently halogen, $C_{1-6}$ alkyl, $C_{2-6}$ alkenyl, $C_{2-6}$ alkynyl, $C(O)R^{300a}$, $OR^{300a}$, $S(O)_2R^{300a}$, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{350}$ substituents;

each $R^{300a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{350}$ substituents;

each $R^{350}$ is independently halogen, CN, $C_{1-6}$ alkyl, $CR^{350a}R^{350a}NR^{350a}R^{350a}$, $C(O)R^{350a}$, $C(O)NR^{350a}R^{350a}$, or $OR^{350a}$;

each $R^{350a}$ is independently H or $C_{1-6}$ alkyl, wherein each $C_{1-6}$ alkyl is optionally and independently substituted with one, two, or three independently selected halogen substituents;

$R^5$ is H, halogen, $C_{1-6}$ alkyl, $C_{2-6}$ alkenyl, $C_{2-6}$ alkynyl, or $OR^{5a}$, wherein the $C_{1-6}$ alkyl, $C_{2-6}$ alkenyl, or $C_{2-6}$ alkynyl is optionally substituted with one or more independently selected halogen substituents;

$R^{5a}$ is H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein the $C_{1-6}$ alkyl, $C_{2-6}$ alkenyl, $C_{2-6}$ alkynyl, 3- to 7-membered carbocyclyl, or 4- to 6-membered heterocyclyl is optionally substituted with one or more independently selected halogen substituents;

$R^6$ is H, halogen, $C_{1-6}$ alkyl, $C_{2-6}$ alkenyl, $C_{2-6}$ alkynyl, or $OR^{6a}$, wherein the $C_{1-6}$ alkyl, $C_{2-6}$ alkenyl, or $C_{2-6}$ alkynyl is optionally substituted with one or more independently selected halogen substituents;

$R^{6a}$ is H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein the $C_{1-6}$ alkyl, $C_{2-6}$ alkenyl, $C_{2-6}$ alkynyl, 3- to 7-membered carbocyclyl, or 4- to 6-membered heterocyclyl is optionally substituted with one or more independently selected halogen substituents;

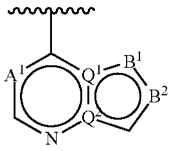 is 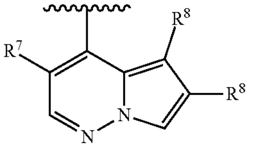 or

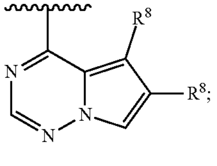

$R^7$ is H, CN, $C_{1-6}$ alkyl, $C_{2-6}$ alkenyl, $C_{2-6}$ alkynyl, $C(O)R^{7a}$, $C(O)NR^{7a}R^{7a}$, $C(O)OR^{7a}$, or $OR^{7a}$, wherein the $C_{1-6}$ alkyl, $C_{2-6}$ alkenyl, or C2-6 alkynyl is optionally substituted with one or more independently selected $R^{70}$ substituents;

each $R^{7a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{70}$ substituents;

each $R^{70}$ is independently halogen, $C_{1-6}$ alkyl, $C_{2-6}$ alkenyl, $C_{2-6}$ alkynyl, $OR^{70a}$, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{75}$ substituents;

each $R^{70a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{75}$ substituents;

each $R^{75}$ is independently halogen, $C_{1-6}$ alkyl, or $OR^{75a}$;

each $R^{75a}$ is independently H or $C_{1-6}$ alkyl;

each $R^8$ is independently H, halogen, CN, $C_{1-6}$ alkyl, $C_{2-6}$ alkenyl, $C_{2-6}$ alkynyl, $C(O)R^{8a}$, $C(O)NR^{8a}R^{8a}$, $C(O)OR^{8a}$, $NR^{8a}R^{8a}$, $NR^{8a}C(O)R^{8a}$, $NR^{8a}C(O)NR^{8a}R^{8a}$, $NR^{8a}C(O)OR^{8a}$, $NR^{8a}S(O)_2R^{8a}$, $OR^{8a}$, $OC(O)R^{8a}$; $OC(O)NR^{8a}R^{8a}$, $SR^{8a}$, $S(O)R^{8a}$, $S(O)NR^{8a}R^{8a}$, $S(O)_2R^{8a}$, $S(O)_2NR^{8a}R^{8a}$, monocyclic 3- to 7-membered carbocyclyl, monocyclic 4- to 6-membered heterocyclyl, or bicyclic 7- to 10-membered heterocyclyl, wherein each $C_{1-6}$ alkyl, $C_{2-6}$ alkenyl, $C_{2-6}$ alkynyl, 3- to 7-membered carbocyclyl, 4- to 6-membered heterocyclyl and 7- to 10-membered heterocyclyl is optionally and independently substituted with one or more independently selected $R^{80}$ substituents;

each $R^{8a}$ is independently H, $C_{1-6}$ alkyl, $C_{2-6}$ alkenyl, $C_{2-6}$ alkynyl, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{80}$ substituents; or any two $R^{8a}$, taken together with their intervening atom(s), independently form a monocyclic 4- to 6-membered heterocyclyl, wherein each 4- to 6-membered heterocyclyl is optionally and independently substituted with one or more independently selected $R^{80}$ substituents;

each $R^{80}$ is independently halogen, CN, $C_{1-6}$ alkyl, $C_{2-6}$ alkenyl, $C_{2-6}$ alkynyl, $C(O)R^{80a}$, $C(O)NR^{80a}R^{80a}$, $C(O)OR^{80a}$, $NR^{80a}R^{80a}$, $NR^{80a}C(O)R^{80a}$, $NR^{80a}C(O)NR^{80a}R^{80a}$, $NR^{80a}C(O)OR^{80a}$, $NR^{80a}S(O)_2R^{80a}$, $OR^{80a}$, $OC(O)R^{80a}$, $OC(O)NR^{80a}R^{80a}$, $SR^{80a}$, $S(O)R^{80a}$, $S(O)NR^{80a}R^{80a}$, $S(O)_2R^{80a}$, $S(O)_2NR^{80a}R^{80a}$, monocyclic 3- to 7-membered carbocyclyl, or monocyclic 4- to 6-membered heterocyclyl, wherein each $C_{1-6}$ alkyl, $C_{2-6}$ alkenyl, $C_{2-6}$ alkynyl, 3- to 7-membered carbocyclyl, and 4- to 6-membered heterocyclyl is optionally and independently substituted with one or more independently selected $R^{85}$ substituents; or any two geminal $R^{80}$, together with the carbon atom to which they are attached, form —C(O)—;

each $R^{80a}$ is independently H, $C_{1-6}$ alkyl, $C_{2-6}$ alkenyl, $C_{2-6}$ alkynyl, monocyclic 3- to 6-membered carbocyclyl, or monocyclic 4- to 6-membered heterocyclyl;

wherein each 4- to 6-membered heterocyclyl independently contains 1 or 2 heteroatoms independently selected from the group consisting of N, O, and S; and wherein each $C_{1-6}$ alkyl, $C_{2-6}$ alkenyl, $C_{2-6}$ alkynyl, 3- to 6-membered carbocyclyl, and 4- to 6-membered heterocyclyl is optionally and independently substituted with one or more independently selected $R^{85}$ substituents;

each $R^{85}$ is independently halogen, $C_{1-6}$ alkyl, or $OR^{85a}$; and each $R^{85a}$ is independently H or $C_{1-6}$ alkyl.

2. The compound of claim 1, wherein the compound is represented by Formula (II):

(II)

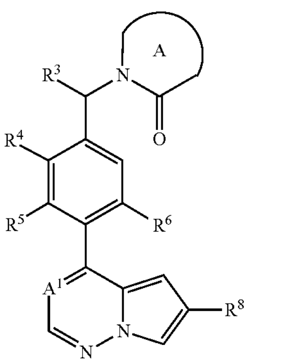

or a pharmaceutically acceptable salt thereof, wherein:

$A^1$ is $CR^7$ or N; and $R^7$ is H.

3. The compound of claim 2, or a pharmaceutically acceptable salt thereof, wherein:

Ring A is a monocyclic 5- or 6-membered heterocyclyl or bicyclic 8- to 10-membered heterocyclyl, wherein Ring A is optionally substituted with one, two, or three independently selected $R^{100}$ substituents;

each $R^{100}$ is independently halogen, CN, $C_{1-6}$ alkyl, $C(O)R^{100a}$, $C(O)NR^{100a}R^{100a}$, $C(O)OR^{100a}$, $NR^{100a}R^{100a}$, $NR^{100a}C(O)R^{100a}$, $NR^{100a}C(O)NR^{100a}R^{100a}$, $NR^{100a}C(O)OR^{100a}$, $NR^{100a}S(O)_2R^{100a}$ $OR^{100a}$, $OC(O)R^{100a}$, $OC(O)NR^{100a}R^{100a}$, $SR^{100a}$, $S(O)R^{100a}$, $S(O)NR^{100a}R^{100a}$, $S(O)_2R^{100a}$, $S(O)_2NR^{100a}R^{100a}$, monocyclic $C_{3-6}$ cycloalkyl, or monocyclic 4- to 6-membered heterocyclyl, wherein each $C_{1-6}$ alkyl, $C_{3-6}$ cycloalkyl, and 4- to 6-membered heterocyclyl is optionally and independently substituted with one, two, or three independently selected $R^{150}$ substituents; or any two $R^{100}$, taken together with their intervening atom(s), independently form a monocyclic 3- to 7-membered carbocyclyl or monocyclic 4- to 6-membered heterocyclyl, wherein each 3- to 7-membered carbocyclyl and 4- to 6-membered heterocyclyl is optionally and independently substituted with one or more independently selected $R^{150}$ substituents;

each $R^{100a}$ is independently H, $C_{1-6}$ alkyl, monocyclic $C_{3-6}$ cycloalkyl, or monocyclic 4- to 6-membered heterocyclyl;

each $R^{150}$ is independently halogen, $C_{1-6}$ alkyl, or $OR^{150a}$, and each $R^{150a}$ is independently H or $C_{1-6}$ alkyl.

4. The compound of claim 3, or a pharmaceutically acceptable salt thereof, wherein Ring A is:

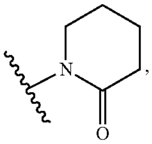,
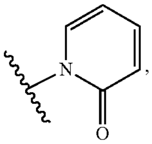,
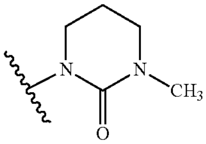,
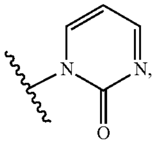
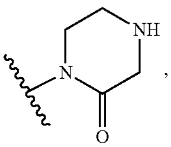,
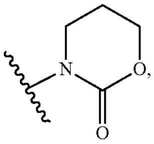
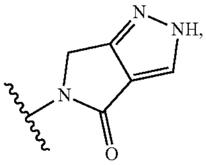
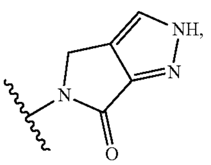
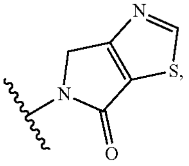
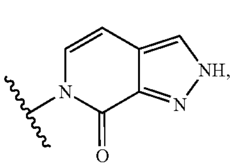
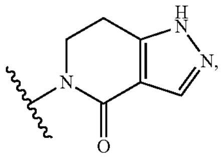
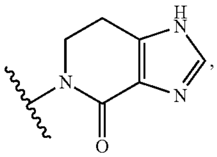,
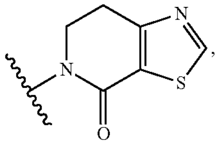,
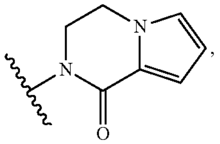
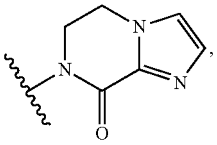, or
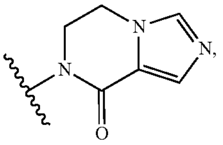

wherein Ring A, when unsubstituted, is optionally substituted with one, two, or three independently selected $R^{100}$ substituents; or wherein Ring A, when monosubstituted, is optionally further substituted with one or two additional independently selected $R^{100}$ substituents.

5. The compound of claim 4, or a pharmaceutically acceptable salt thereof, wherein Ring A is:

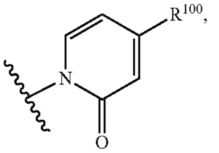
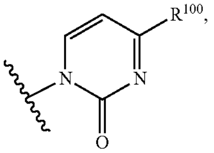

-continued

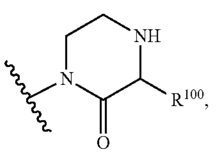 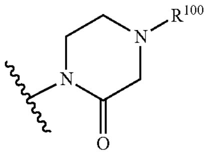 ,

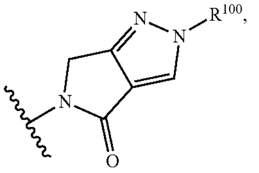 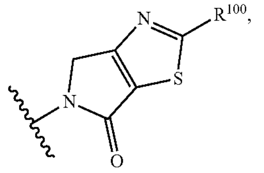

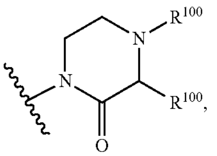 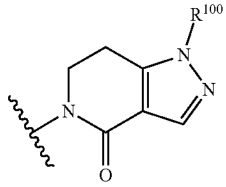 ,

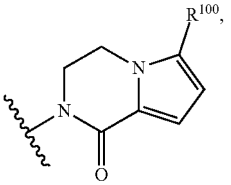 or 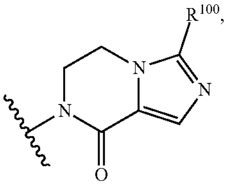

wherein Ring A, when monosubstituted, is optionally further substituted with one or two additional independently selected $R^{100}$ substituents; or wherein Ring A, when disubstituted, is optionally further substituted with one additional $R^{100}$ substituent.

6. The compound of claim 5, or a pharmaceutically acceptable salt thereof, wherein:

each $R^{100}$ is independently halogen, CN, $C_{1-6}$ alkyl, $OR^{100a}$, or monocyclic $C_{3-6}$ cycloalkyl, wherein each $C_{1-6}$ alkyl and $C_{3-6}$ cycloalkyl is optionally and independently substituted with one, two, or three independently selected $R^{150}$ substituents;

each $R^{100a}$ is independently H, $C_{1-6}$ alkyl, monocyclic $C_{3-6}$ cycloalkyl, or monocyclic 4- to 6-membered heterocyclyl; and each $R^{150}$ is independently halogen or $C_{1-6}$ alkyl.

7. The compound of claim 2, or a pharmaceutically acceptable salt thereof, wherein:

$R^4$ is halogen, CN, $C_{1-6}$ alkyl, $OR^{4a}$, or monocyclic $C_{3-6}$ cycloalkyl, wherein the $C_{1-6}$ alkyl or $C_{3-6}$ cycloalkyl is optionally substituted with one, two, or three independently selected $R^{40}$ substituents;

$R^{4a}$ is $C_{1-4}$ alkyl, wherein the $C_{1-4}$ alkyl is optionally substituted with one, two, or three independently selected $R^{40}$ substituents; and each $R^{40}$ is independently halogen.

8. The compound of claim 7, or a pharmaceutically acceptable salt thereof, wherein $R^4$ is $CH_3$, $CHF_2$, $CF_3$, $CH_2CHF_2$, or cyclopropyl.

9. The compound of claim 2, or a pharmaceutically acceptable salt thereof, wherein $R^5$ is H or halogen.

10. The compound of claim 2, or a pharmaceutically acceptable salt thereof, wherein $R^6$ is H or halogen.

11. The compound of claim 2, or a pharmaceutically acceptable salt thereof, wherein:

$R^8$ is H, halogen, CN, $C_{1-6}$ alkyl, $C_{2-6}$ alkenyl, $C_{2-6}$ alkynyl, $C(O)R^{8a}$, $C(O)NR^{8a}R^{8a}$, $NR^{8a}R^{8a}$, $OR^{8a}$, monocyclic $C_{3-6}$ cycloalkyl, monocyclic 4- to 6-membered heterocyclyl, bicyclic 7- to 10-membered heterocyclyl, or phenyl;

wherein the 4- to 6-membered heterocyclyl contains 1 or 2 heteroatoms independently selected from the group consisting of N, O, and S;

wherein the 7- to 10-membered heterocyclyl contains 1, 2, 3, or 4 heteroatoms independently selected from the group consisting of N, O, and S; and wherein the $C_{1-6}$ alkyl, $C_{2-6}$ alkenyl, $C_{2-6}$ alkynyl, $C_{3-6}$ cycloalkyl, 4- to 6-membered heterocyclyl, 7- to 10-membered heterocyclyl, or phenyl is optionally substituted with one, two, or three independently selected $R^{80}$ substituents;

each $R^{8a}$ is independently H, $C_{1-6}$ alkyl, $C_{2-6}$ alkenyl, $C_{2-6}$ alkynyl, monocyclic $C_{3-6}$ cycloalkyl, or monocyclic 4- to 6-membered heterocyclyl, wherein each $C_{1-6}$ alkyl, $C_{2-6}$ alkenyl, $C_{2-6}$ alkynyl, $C_{3-6}$ cycloalkyl, and 4- to 6-membered heterocyclyl is optionally and independently substituted with one, two, or three independently selected $R^{80}$ substituents; or any two $R^{8a}$, taken together with their intervening atom(s), independently form a monocyclic 4- to 6-membered heterocyclyl, wherein each 4- to 6-membered heterocyclyl is optionally and independently substituted with one, two, or three independently selected $R^{80}$ substituents;

each $R^{80}$ is independently halogen, CN, $C_{1-6}$ alkyl, $C_{2-6}$ alkenyl, $C_{2-6}$ alkynyl, $C(O)R^{80a}$, $OR^{80a}$, monocyclic $C_{3-6}$ cycloalkyl, or monocyclic 4- to 6-membered heterocyclyl, wherein each $C_{1-6}$ alkyl, $C_{2-6}$ alkenyl, $C_{2-6}$ alkynyl, $C_{3-6}$ cycloalkyl, and 4- to 6-membered heterocyclyl is optionally and independently substituted with one, two, or three independently selected $R^{85}$ substituents; or any two geminal $R^{80}$, together with the carbon atom to which they are attached, form —C(O)—;

each $R^{80a}$ is independently H, $C_{1-6}$ alkyl, $C_{2-6}$ alkenyl, $C_{2-6}$ alkynyl, monocyclic $C_{3-6}$ cycloalkyl, or monocyclic 4- to 6-membered heterocyclyl, wherein each 4- to 6-membered heterocyclyl independently contains 1 or 2 heteroatoms independently selected from the group consisting of N, O, and S;

each $R^{85}$ is independently halogen or $OR^{85a}$, and each $R^{85a}$ is independently H or $C_{1-6}$ alkyl.

12. The compound of claim 11, or a pharmaceutically acceptable salt thereof, wherein $R^8$ is H, F, Br, CN, $CH_2$-tetrahydropyran-4-yl, $C(O)N(CH_3)_2$, C(O)-azetidin-1-yl, C(O)-piperazin-1-yl, C(O)-morpholin-4-yl, $N(CH_3)CH_2CH_2OCH_3$, $OCH_2CH_2OCH_3$, $OCH(CH_3)OCH_3$, cyclopropyl, azetidinyl, oxetanyl, tetrahydrofuranyl, pyrrolidinyl, piperidinyl, 3,6-dihydro-2H-pyranyl, 3,6-dihydro-2H-thiopyranyl, piperazinyl, morpholinyl, 3,6-diazabicyclo[3.1.1]heptanyl, octahydropyrrolo[1,2-a]pyrazinyl, 4,5,6,7-tetrahydropyrazolo[1,5-a]pyrazinyl, 5,6,7,8-tetrahydroimidazo[1,2-a]pyrazinyl, phenyl, pyrazolyl, oxazolyl, isothiazolyl, thiazolyl, 1,2,3-triazinyl, pyridinyl, pyrazinyl, or pyrimidinyl.

13. The compound of claim 11, or a pharmaceutically acceptable salt thereof, wherein:

each $R^{80}$ is independently halogen, CN, $C_{1-3}$ alkyl, $C(O)R^{80a}$, $OR^{80a}$, monocyclic $C_{3-6}$ cycloalkyl, or monocyclic 4- to 6-membered heterocyclyl;

wherein each 4- to 6-membered heterocyclyl independently contains 1 or 2 heteroatoms independently selected from the group consisting of N and O; and wherein each $C_{1-6}$ alkyl, $C_{3-6}$ cycloalkyl, and 4- to 6-membered heterocyclyl is optionally and independently substituted with one, two, or three independently selected $R^{85}$ substituents; or any two geminal $R^{80}$, together with the carbon atom to which they are attached, form —C(O)—;

each $R^{80a}$ is independently $C_{1-4}$ alkyl or $C_{2-4}$ alkenyl;

each $R^{85}$ is independently F or $OR^{85a}$, and each $R^{85a}$ is independently H or $C_{1-3}$ alkyl.

14. The compound of claim 1, wherein the compound is represented by Formula (IIA) or Formula (IIB):

(IIA)

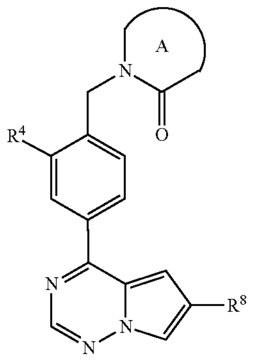

or (IIB)

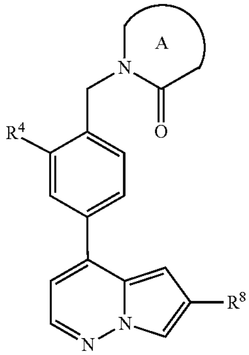

or a pharmaceutically acceptable salt thereof, wherein:

Ring A is a monocyclic 5- or 6-membered heterocyclyl or bicyclic 9- or 10-membered heterocyclyl, wherein Ring A is optionally substituted with one or two independently selected $R^{100}$ substituents;

each $R^{100}$ is independently $C_{1-6}$ alkyl or monocyclic $C_{4-6}$ cycloalkyl, wherein each $C_{1-6}$ alkyl and $C_{4-6}$ cycloalkyl is optionally and independently substituted with one, two, or three independently selected $R^{150}$ substituents;

each $R^{150}$ is independently halogen;

$R^4$ is $C_{1-4}$ alkyl, wherein the $C_{1-4}$ alkyl is optionally substituted with one, two, or three independently selected $R^{40}$ substituents;

each $R^{40}$ is independently halogen;

$R^8$ is H, halogen, $C_{1-6}$ alkyl, $C(O)NR^{8a}R^{8a}$, $OR^{8a}$, or monocyclic 5- or 6-membered heteroaryl;

wherein the 5- or 6-membered heteroaryl contains 1 or 2 heteroatoms independently selected from the group consisting of N, O, and S; and wherein the $C_{1-6}$ alkyl or 5- or 6-membered heteroaryl is optionally substituted with one, two, or three independently selected $R^{80}$ substituents;

each $R^{8a}$ is independently $C_{1-6}$ alkyl, wherein each $C_{1-6}$ alkyl is optionally and independently substituted with one, two, or three independently selected $R^{80}$ substituents;

each $R^{80}$ is independently halogen, $C_{1-4}$ alkyl, or $OR^{80a}$; and each $R^{80a}$ is independently H or $C_{1-3}$ alkyl.

15. The compound of claim 14, or a pharmaceutically acceptable salt thereof, wherein:

Ring A is:

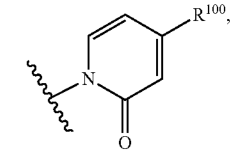

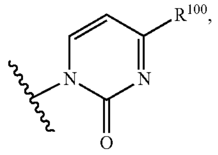

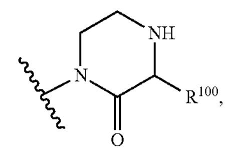

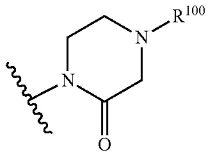

,

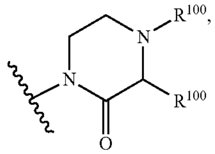

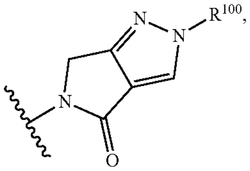

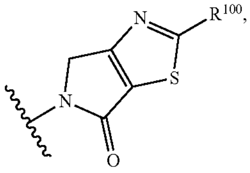

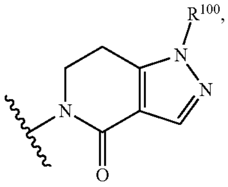

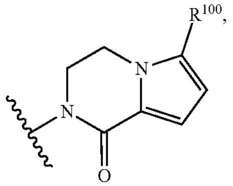

or

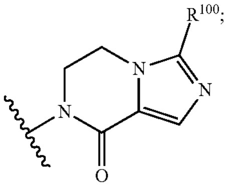

each $R^{100}$ is independently $C_{1-6}$ alkyl or monocyclic $C_{4-6}$ cycloalkyl, wherein each $C_{1-6}$ alkyl and $C^{4-6}$ cycloalkyl is optionally and independently substituted with one, two, or three independently selected $R^{150}$ substituents; and each $R^{150}$ is independently halogen.

16. The compound of claim 15, or a pharmaceutically acceptable salt thereof, wherein:

$R^8$ is H, $C(O)NR^{8a}R^{8a}$, $OR^{8a}$, or monocyclic 5-membered heteroaryl;

wherein the 5-membered heteroaryl contains 1 or 2 heteroatoms independently selected from the group consisting of N, O, and S; and wherein the 5-membered heteroaryl is optionally substituted with one, two, or three independently selected $R^{80}$ substituents;

each $R^{8a}$ is independently $C_{1-6}$ alkyl, wherein each $C_{1-6}$ alkyl is optionally and independently substituted with one, two, or three independently selected $R^{80}$ substituents;

each $R^{80}$ is independently halogen, $C_{1-4}$ alkyl, or $OR^{80a}$; and each $R^{80a}$ is independently H or $C_{1-3}$ alkyl.

17. A pharmaceutical composition comprising a pharmaceutically acceptable excipient and a compound of claim 1, or a pharmaceutically acceptable salt thereof.

18. A method for inhibiting Bruton's tyrosine kinase (BTK) activity in a subject, wherein the method comprises administering to the subject in need thereof an effective amount of a compound of claim 1, or a pharmaceutically acceptable salt thereof.

19. The method of claim 18, wherein the subject has a disorder responsive to the inhibition of Bruton's tyrosine kinase (BTK) activity selected from the group consisting of atopic dermatitis, an autoimmune disorder, leukemia, lymphoma, multiple sclerosis, rheumatoid arthritis, and systemic lupus erythematosus.

* * * * *